United States Patent
Kawanishi et al.

(10) Patent No.: US 7,168,300 B2
(45) Date of Patent: Jan. 30, 2007

(54) GASOLINE IDENTIFICATION SYSTEM AND METHOD FOR IDENTIFYING GASOLINE TYPE

(75) Inventors: Toshiaki Kawanishi, Ageo (JP); Kiyoshi Yamagishi, Ageo (JP); Takayuki Takahata, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 10/529,796

(22) PCT Filed: Sep. 30, 2003

(86) PCT No.: PCT/JP03/12505

§ 371 (c)(1),
(2), (4) Date: Mar. 30, 2005

(87) PCT Pub. No.: WO2004/029615

PCT Pub. Date: Apr. 8, 2004

(65) Prior Publication Data

US 2006/0243248 A1   Nov. 2, 2006

(30) Foreign Application Priority Data

Sep. 30, 2002  (JP) ............................. 2002-286669

(51) Int. Cl.
   *G01N 25/18*   (2006.01)
(52) U.S. Cl. ................. 73/61.46; 123/1 A; 123/406.31
(58) Field of Classification Search ................. 123/1 A, 123/406.3, 406.31; 73/61.46
See application file for complete search history.

(56) References Cited

U.S. PATENT DOCUMENTS 4,589,277 A * 5/1986 Collins et al. ............. 73/61.61

(Continued)

FOREIGN PATENT DOCUMENTS

JP    4-76451 A    3/1992

(Continued)

OTHER PUBLICATIONS

Sanma, Norio et al., "Capacitance-Type Alcohol Sensor", *The Society of Automotive Engineers of Japan*, Annual Congress Preliminary Printing Collection 936, Oct. 1993, pp. 257-260 with English translation.

*Primary Examiner*—Erick Solis
(74) *Attorney, Agent, or Firm*—The Webb Law Firm

(57) ABSTRACT

The types of gasolines having different distillation characteristics and various compositions are identified accurately and rapidly. A pulse voltage is applied for a predetermined time to a liquid type identifying sensor heater including a heater and an identifying liquid temperature sensor provided in the vicinity of the heater and an identified gasoline is heated by the heater and the liquid type is identified with a voltage output difference V0 corresponding to a temperature difference between an initial temperature and a peak temperature in the identifying liquid temperature asensor. Furthermore, a gasoline is introduced between electrodes of an alcohol concentration detecting sensor, and a change in a specific inductive capacity of the gasoline between the electrodes is measured with an oscillation frequency thereby detecting an alcohol concentration in the gasoline. Moreover, based on the alcohol concentration detected by the alcohol concentration detecting device, correcting liquid type identification data in the identification control portion on the basis of alcohol concentration data which are prestored in the identification control portion, thereby identifying a liquid type.

34 Claims, 31 Drawing Sheets

U.S. PATENT DOCUMENTS

| | | | | |
|---|---|---|---|---|
| 5,005,402 A | * | 4/1991 | Pischinger et al. | 324/663 |
| 5,182,942 A | * | 2/1993 | Hartel et al. | 73/61.46 |
| 5,594,163 A | | 1/1997 | Suzuki | |
| 6,588,253 B2 | * | 7/2003 | Lambert et al. | 73/53.01 |

FOREIGN PATENT DOCUMENTS

| | | |
|---|---|---|
| JP | 05-223733 A | 8/1993 |
| JP | 7-306172 A | 11/1995 |
| JP | 11-153561 A | 6/1999 |

* cited by examiner

GASOLINE IDENTIFICATION SYSTEM AND METHOD FOR IDENTIFYING GASOLINE TYPE

BACKGROUND OF THE INVENTION

1. Field of the Invention

The present invention relates to an apparatus and method for identifying the liquid type of a gasoline.

2. Description of Related Art

Conventionally, the exhaust gas of a car contains pollutants such as unburned hydrocarbon (HC), an NOx gas and an SOx gas. In order to reduce the pollutants, therefore, S in a gasoline is removed for the Sox or unburned HC is burned by a catalyst, for example.

More specifically, as shown in FIG. 28, a car system 100 takes air in through an automatic element (filter) 102 and feeds the air into an engine 106 through an air flow sensor 104. Moreover, the car system 100 feeds a gasoline in a gasoline tank 108 into the engine 106 through a gasoline pump 110.

Based on the result of the detection of an A/F sensor 112, the injection of the fuel in the engine 106 is controlled by a fuel injection control device 114 in order to have a predetermined theoretical air fuel ratio.

For an exhaust gas fed from the engine 106, hydrocarbon (HC) in the exhaust gas is burned by a catalytic device 116 and is then discharged as the exhaust gas through an oxygen concentration sensor 118.

In such a car system, gasolines sold all over the world include various gasolines having different distillation characteristics (different easinesses of evaporation) as shown in FIG. 29.

More specifically, FIG. 29 shows the distillation characteristics of gasolines, illustrating a relationship between a percentage and a temperature, and an axis of abscissa of 50% (T50) indicates a temperature at which 50% of each gasoline evaporates, for example.

As shown in FIG. 29, for example, a gasoline A2 represents the heaviest gasoline (which rarely evaporates) and a gasoline No. 7 represents the lightest gasoline (which easily evaporates) with respect to a standard gasoline No. 3.

As shown in the following Table 1, accordingly, in the case in which the heavier gasoline A2 is used in a car regulated to have a theoretical air fuel ratio with the standard gasoline No. 3, for example, the amount of HC in an exhaust gas is small and a torque becomes insufficient, particularly, at time of engine starting in which an engine and a catalytic device do not warm up.

To the contrary, in the case in which the lighter gasoline No. 7 is used, the torque is insufficient and the theoretical air fuel ratio is exceeded. As a result, the amount of the HC in the exhaust gas is increased, particularly, at time of the engine starting in which the engine and the catalytic device do not warm up, which is not preferable because an environment is greatly influenced.

TABLE 1

| Regulated gasoline | Used gasoline | Torque | Exhaust gas (HC) |
|---|---|---|---|
| No. 3 | No. 3 | ○ | ○ |
| No. 3 | A2 | X | ○ |
| No. 3 | No. 7 | ○ | X |

The present inventors have proposed a fluid identifying method in Japanese Laid-Open Patent Publication No. Hei 11(1999)-153561 (particularly see paragraphs (0042) to (0049)) (which will be hereinafter referred to as "Patent Document 1"). In this method, a heating member is caused to generate heat by carrying electricity, a temperature detector is heated through the heat generation, a heat transfer from the heating member to the temperature detector is thermally influenced through a fluid to be identified, and the type of the identified fluid is distinguished based on an electrical output corresponding to the electric resistance of the temperature detector. In this method, the electricity is periodically carried to the heating member.

In the fluid identifying method, however, it is necessary to periodically carry the electricity to the heating member (in a multipulse). For this reason, a long time is required for the identification so that it is hard to identify a fluid instantaneously. In this method, moreover, it is possible to identify a fluid based on a central value for substances having very different characteristics such as water, air and oil. However, it is hard to identify the gasolines having very close characteristics to each other accurately and rapidly.

Conventionally, a so-called high-octane gasoline having an octane value increased such as lead or a benzene based compound, or a gasoline into which an antiknocking agent such as methyl tertiary butyl ether or methyl-t-butyl ether (MTBE) is mixed has been used for a car or the like in order to prevent knocking, for example.

However, there is a possibility that the lead, the benzene based compound or the like might influence an environment. Moreover, it is said that the methyl tertiary butyl ether or the methyl-t-butyl ether (MTBE) is cancer-causing. For this reason, it has been desired to develop the high-octane gasoline and an antiknocking agent in place of the antiknocking agent constituted by the methyl tertiary butyl ether or the methyl-t-butyl ether (MTBE).

Therefore, it has been proposed that alcohol, for example, ethanol is added, as the antiknocking agent, in an amount of approximately 10 to 15% to a gasoline.

However, such ethanol is added so that a torque is reduced. Therefore, it is necessary to cause the torque to be constant by excessively adding a gasoline corresponding to the amount of addition of the ethanol.

In the case in which the alcohol is contained in the gasoline in the identification of the liquid type of the gasoline as described above, furthermore, liquid type identification data are influenced. As a result, it is hard to identify the liquid type accurately and rapidly.

For this reason, it has been desired to detect the concentration of alcohol contained in a gasoline.

As a method for detecting the concentration of alcohol, conventionally, an optical alcohol concentration measuring apparatus for detecting the concentration of alcohol by utilizing the refractive index of a light has been disclosed as in Japanese Laid-Open Patent Publication No. Hei 5 (1993)-223733 (see paragraphs (0017) to (0030) and FIG. 1) (whichwillbehereinafter referred to as "Patent Document 2").

More specifically, in an optical alcohol concentration measuring apparatus 200 in the Patent Document 2, as shown in FIG. 30, a light which is transmitted from a first light emitting portion 202 through a liquid and has a wavelength with such a property that an absorption into alcohol such as ethanol is hard to perform is received by a first light receiving portion 204 and a detection signal corresponding to an alcohol concentration in the liquid is output.

Moreover, a light, which is transmitted from a second light emitting portion 206 through the liquid and has another wavelength with such a property that the absorption into the alcohol is easy, is received by a second light receiving portion 208 and a detection signal corresponding to the alcohol concentration in the liquid is output.

Consequently, in a measuring portion 210, the detection signal sent from the first light receiving portion 204 is compared with the detection signal sent from the second light receiving portion 208 and the alcohol concentration in the liquid is measured.

As described in "Electrostatic Capacitance Type Alcohol Concentration Sensor" (see Norio Sanma, Ikuo Hayashi, Ichiro Hosotani, The Society of Automotive Engineers of Japan, Annual Congress Preliminary Printing Collection 936, 1993-10, pages 257 to 260) (which will be herein after referred to as "Non-Patent Document 1"), conventionally, an electrostatic capacitance type alcohol concentration sensor has been proposed.

In the Non-Patent Document 1, there has been proposed a method for measuring the concentration of methanol mixed into a gasoline from an electrostatic capacitance between electrodes at an oscillation frequency by utilizing a difference in a specific inductive capacity between the gasoline and the methanol (the gasoline has a specific inductive capacity of 2 and the methanol has a specific inductive capacity of 33.6), thereby detecting the concentration of the methanol.

An electrostatic capacitance type alcohol concentration sensor 300 according to the Non-Patent Document 1 has such a structure that an outer electrode 304 and a center electrode 306 are attached through an insulating resin 308 into a housing 302 as shown in FIG. 31.

Since the optical alcohol concentration measuring apparatus according to the Patent Document 2 utilizes a transmitted light, however, it is easily influenced by the composition of a gasoline. For example, in the case in which the gasoline is not transparent due to an impurity, moreover, a measurement cannot be carried out or an accurate measurement cannot be performed.

In the electrostatic capacitance type alcohol concentration sensor utilizing an electrostatic capacitance according to the Non-Patent Document 1, furthermore, a moisture is apt to enter alcohol and a short circuit is generated between electrodes if the moisture, an electrolyte or the like is present between the electrodes. Accordingly, an insulating treatment for the surface of the electrode is required and a structure thereof is complicated.

In this case, an electrostatic capacitance $C_s$ is expressed in the following equation.

$$C_s = \epsilon_0 (S/D) (\epsilon\, ra(\alpha/100) + \epsilon rg(1-\alpha/100)) \quad \text{Equation 1}$$

Herein, S represents an opposed area of an electrode, D represents a distance between the electrodes, $\epsilon_0$ represents a specific inductive capacity of a vacuum (8.854 E–12 F/m), $\epsilon$ ra represents a specific inductive capacity of alcohol, $\epsilon$ rg represents a specific inductive capacity of a gasoline, and a represents an alcohol concentration (%).

As is apparent from the Equation, accordingly, it is preferable to increase the opposed area of the electrode to increase the electrostatic capacitance Cs in order to obtain the excellent results of the measurement. When the opposed area of the electrode is thus increased, however, the size of the electrostatic capacitance type alcohol concentration sensor itself is increased as in the Non-Patent Document 1. For this reason, handling, an application to a car and the like are also restricted in respect of a design.

In the electrostatic capacitance type alcohol concentration sensor according to the Non-Patent Document 1, further-more, the sensor is to be connected to a body of a gasoline piping in a car or the like, for example. However, a noise such as an electromagnetic wave or the like which is generated from the body influences an alcohol-concentration detecting circuit so that an accurate measurement cannot be carried out.

For this reason, an insulating structure is added to the connecting portion of the sensor and the piping or the whole large-sized sensor is to be put in an insulating shield container. Consequently, the apparatus becomes complicated and large-sized.

In consideration of such circumstances, it is an object of the present invention to provide an apparatus and method for identifying the liquid type of a gasoline which can identify the type of a gasoline accurately and rapidly by detecting an alcohol concentration in each of gasolines having different distillation characteristics and various compositions and correcting liquid type identification data on the gasolines based on a result.

Moreover, it is an object of the present invention to provide an apparatus for identifying the liquid type of a gasoline, comprising an alcohol concentration detecting device which is small-sized and compact, can be installed everywhere and can have the degree of freedom of a design, has an excellent insulation between electrodes and is not influenced by a moisture, can carry out shielding in order not to be influenced by an electromagnetic wave generated from a body of a car or the like, and furthermore, can execute an accurate measurement for the alcohol concentration, and a method for identifying the liquid type of a gasoline.

Furthermore, it is an object of the present invention to provide an apparatus and method for identifying the liquid type of the gasoline of a car using the apparatus and method for identifying the liquid type of a gasoline.

In addition, it is an object of the present invention to provide an apparatus and method for reducing the exhaust gas of a car using the apparatus and method for identifying the liquid type of a gasoline which can efficiently reduce the exhaust gas and can enhance a mileage.

SUMMARY OF THE INVENTION

The present invention has been made to solve the problems of the prior art and to attain the objects described above, and provides an apparatus for identifying a liquid type of a gasoline, comprising:

a gasoline liquid type identifying chamber for causing an identified gasoline introduced into the liquid type identifying apparatus body to stay temporarily;

a liquid type identifying sensor heater provided in the gasoline liquid type identifying chamber; and a liquid temperature sensor provided in the gasoline liquid type identifying chamber apart from the liquid type identifying sensor heater at a constant interval;

the liquid type identifying sensor heater including a heater and an identifying liquid temperature sensor provided in the vicinity of the heater, the apparatus further comprising an identification control portion for applying a pulse voltage to the liquid type identifying sensor heater for a predetermined time, heating the identified gasoline staying temporarily in the gasoline liquid type identifying chamber by the heater and identifying the liquid type with a voltage output difference V0 corresponding to a temperature difference between an initial temperature and a peak temperature in the identifying liquid temperature sensor, and an alcohol content detecting chamber, the alcohol content detecting chamber being provided with an alcohol concentration detecting device in which an alcohol concentration in the gasoline is detected by introducing a gasoline between electrodes of an alcohol concentration detecting sensor and by measuring a change in a specific inductive capacity of the gasoline between the electrodes with an oscillation frequency, wherein based on the alcohol concentration detected by the alcohol concentration detecting device, liquid type identification data in the identification control portion being corrected on the basis of alcohol concentration data which are prestored in the identification control portion, thereby identifying a liquid type.

Moreover, the present invention provides a method for identifying a liquid type of a gasoline, comprising the steps of:

applying a pulse voltage for a predetermined time to a liquid type identifying sensor heater including a heater and an identifying liquid temperature sensor provided in the vicinity of the heater, heating an identified gasoline by the heater, and identifying the liquid type with a voltage output difference V0 corresponding to a temperature difference between an initial temperature and a peak temperature in the identifying liquid temperature sensor;

introducing a gasoline between electrodes of an alcohol concentration detecting sensor, and measuring a change in a specific inductive capacity of the gasoline between the electrodes with an oscillation frequency thereby detecting an alcohol concentration in the gasoline; and based on the alcohol concentration detected by the alcohol concentration detecting device, correcting liquid type identification data in the identification control portion on the basis of alcohol concentration data which are prestored in the identification control portion, thereby identifying a liquid type.

By such a structure, it is sufficient that the pulse voltage is applied for the predetermined time. Consequently, it is possible to identify the type of a gasoline accurately and rapidly through heating for a short time without carrying out the heating to such a temperature as to ignite the gasoline.

More specifically, there are utilized the correlation of the kinetic viscosity of the gasoline with a sensor output, a natural convection, and furthermore, an applied voltage having one pulse. Therefore, it is possible to identify the type of the gasoline accurately and rapidly.

In addition, it is possible to detect an alcohol concentration in the gasoline and to correct liquid type identification data on the gasoline based on a result, thereby identifying the type of the gasoline accurately and rapidly.

Furthermore, the present invention is characterized in that the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $V0=V2-V1$.

By such a structure, it is possible to accurately obtain the voltage output difference V0 based on the average value of the sampling at the predetermined number of times for the applied voltage having one pulse. Consequently, it is possible to identify the type of a gasoline accurately and rapidly.

Moreover, the apparatus for identifying a liquid type of a gasoline according to the present invention is characterized in that, in accordance with calibration curve data to be a correlation of a voltage output difference with a temperature for a predetermined reference gasoline prestored in the identification control portion, the identification control portion is constituted to identify a type of a gasoline with the voltage output difference V0 obtained for the identified gasoline.

In addition, the method for identifying a liquid type of a gasoline according to the present invention is characterized in that, in accordance with calibration curve data to be a correlation of a voltage output difference with a temperature for a predetermined reference gasoline which is prestored, a type of a gasoline is identified with the voltage output difference V0 obtained for the identified gasoline.

By such a structure, in accordance with the calibration curve data to be the correlation of the voltage output difference with the temperature for the predetermined reference gasoline which is prestored, the type of the gasoline is identified with the voltage output difference V0 obtained for the identified gasoline. Therefore, it is possible to identify the type of the gasoline more accurately and rapidly.

Furthermore, the apparatus for identifying a liquid type of a gasoline according to the present invention is characterized in that the identification control portion is constituted to correlate a liquid type voltage output Vout for the voltage output difference V0 at a measuring temperature of the identified gasoline with an output voltage for a voltage output difference at a measuring temperature for a predetermined threshold reference gasoline and to thus carry out a correction.

Moreover, the method for identifying a liquid type of a gasoline according to the present invention is characterized in that a liquid type voltage output Vout for the voltage output difference V0 at a measuring temperature of the identified gasoline is correlated with an output voltage for a voltage output difference at a measuring temperature for a predetermined threshold reference gasoline and is thus corrected.

By such a structure, the liquid type voltage output Vout for the voltage output difference V0 at the measuring temperature of the identified gasoline is correlated with the output voltage for the voltage output difference at the measuring temperature for the predetermined threshold reference gasoline and is thus corrected. Consequently, it is possible to eliminate the influence of the temperature on the voltage output difference V0, thereby giving the correlation of the liquid type voltage output Vout with the characteristics of the gasoline more accurately. Thus, it is possible to identify the type of the gasoline further accurately and rapidly.

Furthermore, the present invention is characterized in that the liquid type identifying sensor heater is a laminated liquid type identifying sensor heater in which a heater and an identifying liquid temperature sensor are laminated through an insulating layer.

By such a structure, a mechanism portion for carrying out a mechanical operation is not present. Therefore, a defective operation can be prevented from being caused by a deterioration with the passage of time, foreign matters in the gasoline or the like. Thus, it is possible to identify the liquid type of the gasoline accurately and rapidly.

In addition, the sensor portion can be constituted to be very small-sized. Consequently, it is possible to identify the liquid type of the gasoline accurately with a very excellent thermal responsiveness.

Moreover, the present invention is characterized in that the heater and the identifying liquid temperature sensor in the liquid type identifying sensor heater are constituted to come in contact with the identified gasoline through a metallic fin, respectively.

By such a structure, the heater and the identifying liquid temperature sensor in the liquid type identifying sensor heater do not directly come in contact with the identified gasoline. Therefore, a defective operation can be prevented from being caused by a deterioration with the passage of time, foreign matters in the gasoline or the like. Thus, it is possible to identify the liquid type of the gasoline accurately and rapidly.

Furthermore, the present invention is characterized in that the liquid temperature sensor is constituted to come in contact with the identified gasoline through the metallic fin.

By such a structure, the liquid temperature sensor does not directly come in contact with the identified gasoline. Therefore, a defective operation can be prevented from being caused by a deterioration with the passage of time, foreign matters in the gasoline or the like. Thus, it is possible to identify the liquid type of the gasoline accurately and rapidly.

Moreover, the present invention is characterized in that the alcohol concentration detecting sensor comprises an alcohol concentration detecting sensor body including a base material resin film, an electrode wiring pattern formed on the base material resin film, and an insulating resin covering a surface of the electrode wiring pattern.

By such a structure, it is possible to reduce a distance between the electrodes by using the electrode wiring pattern formed on the base material resin film. As is apparent from Equation 2 which will be described below, therefore, an electrostatic capacitance $C_s$ can be increased so that the excellent result of the measurement can be obtained.

In addition, the alcohol concentration detecting sensor is constituted by the base material resin film, the electrode wiring pattern formed on the base material resin film, and the insulating resin covering the surface of the electrode wiring pattern. Therefore, the sensor itself is flexible, thin, very small and compact, and can be installed everywhere so that the degree of freedom of a design can be increased.

Furthermore, the surface of the electrode wiring pattern is covered with the insulating resin. Therefore, an insulation between the electrodes is excellent and is not influenced by a moisture, and shielding can be carried out in order to prevent the influence of an electromagnetic wave generated from the body of a car or the like. Furthermore, an accurate measurement for the alcohol concentration can be executed.

Moreover, the electrode does not directly come in contact with the gasoline. Therefore, a defective operation can be prevented from being caused by a deterioration with the passage of time, foreign matters in the gasoline or the like. Thus, it is possible to detect the alcohol concentration accurately and rapidly.

In addition, the present invention is characterized in that the alcohol concentration detecting sensor body is stuck onto a substrate.

By such a structure, the alcohol concentration detecting sensor body is stuck onto the substrate. Therefore, it is easy to assemble and attach the alcohol concentration detecting sensor body into the apparatus.

Moreover, the present invention is characterized in that the electrode wiring pattern is obtained by selectively etching a conductive metallic foil laminated on one of surfaces of the base material resin film, thereby forming a wiring pattern taking a predetermined shape.

By such a structure, it is possible to obtain an electrode wiring pattern having a very small distance between the electrodes, for example, within a range of approximately 5 µm to 50 µm by etching. Therefore, the electrostatic capacitance $C_s$ can be increased so that the excellent result of the measurement can be obtained.

In addition, the sensor itself is thin, very small and compact, and can be installed everywhere so that the degree of freedom of a design can be increased.

Furthermore, the present invention is characterized in that the alcohol concentration detecting sensor comprises a substrate, an electrode wiring pattern formed on the substrate, and an insulating coat covering a surface of the electrode wiring pattern.

By such a structure, it is possible to reduce a distance between the electrodes by using the electrode wiring pattern formed on the substrate. As is apparent from the Equation 2 which will be described below, therefore, an electrostatic capacitance $C_s$ can be increased so that the excellent result of the measurement can be obtained.

In addition, the alcohol concentration detecting sensor is constituted by the substrate, the electrode wiring pattern formed on the substrate, and the insulating coat covering the surface of the electrode wiring pattern. Therefore, the sensor itself is thin, very small and compact, and can be installed everywhere so that the degree of freedom of a design can be increased.

Furthermore, the surface of the electrode wiring pattern is covered with the insulating coat. Therefore, an insulation between the electrodes is excellent and is not influenced by a moisture, and shielding can be carried out in order to prevent the influence of an electromagnetic wave generated from the body of a car or the like. Furthermore, an accurate measurement for the alcohol concentration can be executed.

Moreover, the electrode does not directly come in contact with the gasoline. Therefore, a defective operation can be prevented from being caused by a deterioration with the passage of time, foreign matters in the gasoline or the like. Thus, it is possible to detect the alcohol concentration accurately and rapidly.

In addition, the substrate is provided. Therefore, it is easy to assemble and attach the alcohol concentration detecting sensor into the apparatus.

Moreover, the present invention is characterized in that the electrode wiring pattern is obtained by selectively etching a conductive metallic thin film formed on one of surfaces of the substrate by sputtering, thereby forming a wiring pattern taking a predetermined shape.

By such a structure, it is possible to obtain an electrode wiring pattern having a thickness of 0.1 to 5 µm by sputtering at a very small distance between the electrodes, for example, within a range of approximately 5 µm to 50 µm by the sputtering. Therefore, the electrostatic capacitance CS can be increased so that the excellent result of the measurement can be obtained.

In addition, the sensor itself is thin, very small and compact, and can be installed everywhere so that the degree of freedom of a design can be increased.

Furthermore, the present invention is characterized in that the insulating coat is formed by chemical vapor deposition (CVD).

By such a structure, it is possible to obtain, by the chemical vapor deposition (CVD), a very minute and thin insulating coat such as $SiO_2$, $Al_2O_3$ and the like, which is not influenced by the liquid to be inspected such as a gasoline or alcohol. Thus, the sensor itself can be thin, very small and compact.

Moreover, the present invention is characterized in that the electrode wiring pattern has such a shape that positive and negative electrodes which are comb-toothed are alternately intricate.

By such a structure, the positive and negative electrodes which are comb-toothed are formed to be alternately intricate. Therefore, the electrodes having a very small distance therebetween can be provided to be compact as a whole.

Accordingly, it is possible to obtain an electrode wiring pattern having a very small distance between the electrodes, for example, within a range of approximately 5 µm to 50 µm by etching and sputtering, respectively. Therefore, the electrostatic capacitance $C_s$ can be increased so that the excellent result of the measurement can be obtained.

In addition, the sensor itself is thinner, much smaller and more compact, and can be installed everywhere so that the degree of freedom of a design can be increased.

Furthermore, the present invention provides an apparatus for identifying a liquid type of a gasoline of a car, wherein any of the apparatuses for identifying a liquid type of a gasoline is provided in a gasoline tank or on an upstream side or a downstream side of a gasoline pump.

In addition, the present invention provides a method for identifying a liquid type of a gasoline of a car, comprising the step of:

identifying a type of a gasoline in a gasoline tank or on an upstream side or a downstream side of a gasoline pump by using any of the methods for identifying a liquid type of a gasoline.

By such a structure, it is possible to identify the type of a gasoline accurately and rapidly in a car.

Moreover, the present invention provides an apparatus for reducing an exhaust gas of a car, comprising:

any of the apparatuses for identifying a liquid type of a gasoline which is provided in a gasoline tank or on an upstream side or a downstream side of a gasoline pump; and an ignition timing control device for regulating an ignition timing based on the type of the gasoline which is identified by the apparatus for identifying a liquid type of a gasoline.

Furthermore, the present invention provides a method for reducing an exhaust gas of a car, comprising the steps of:

identifying a type of a gasoline in a gasoline tank or on an upstream side or a downstream side of a gasoline pump by using any of the methods for identifying a liquid type of a gasoline, and regulating an ignition timing based on the type of the gasoline which is identified by the apparatus for identifying a liquid type of a gasoline.

By such a structure, an ignition timing can be regulated based on the result of the identification of the type of the gasoline. Therefore, it is possible to obtain a proper ignition timing corresponding to the type of the gasoline.

Accordingly, it is also possible to reduce the amount of HC in an exhaust gas and to enhance a mileage without decreasing a torque, particularly, at time of engine starting in which an engine and a catalytic device do not warm up.

Moreover, the present invention provides an apparatus for reducing an exhaust gas of a car, comprising:

any of the apparatuses for identifying a liquid type of a gasoline which is provided in a gasoline tank or on an upstream side or a downstream side of a gasoline pump; and a gasoline compression control device for regulating a compressibility of the gasoline based on the type of the gasoline which is identified by the apparatus for identifying a liquid type of a gasoline.

In addition, the present invention provides a method for reducing an exhaust gas of a car, comprising the steps of:

identifying a type of a gasoline in a gasoline tank or on an upstream side or a downstream side of a gasoline pump by using any of the methods for identifying a liquid type of a gasoline; and regulating a compressibility of the gasoline based on the type of the gasoline which is identified by the apparatus for identifying a liquid type of a gasoline.

By such a structure, the compressibility of the gasoline can be regulated based on the result of the identification of the type of the gasoline. Therefore, it is possible to obtain a proper compressibility of the gasoline corresponding to the type of the gasoline.

Accordingly, it is also possible to reduce the amount of HC in an exhaust gas and to enhance a mileage without decreasing a torque, particularly, at time of engine starting in which an engine and a catalytic device do not warm up.

BEST MODE FOR CARRYING OUT DETAILED DESCRIPTION OF THE INVENTION

Embodiments (examples) of the present invention will be described below in more detail with reference to the drawings.

Figure 1:
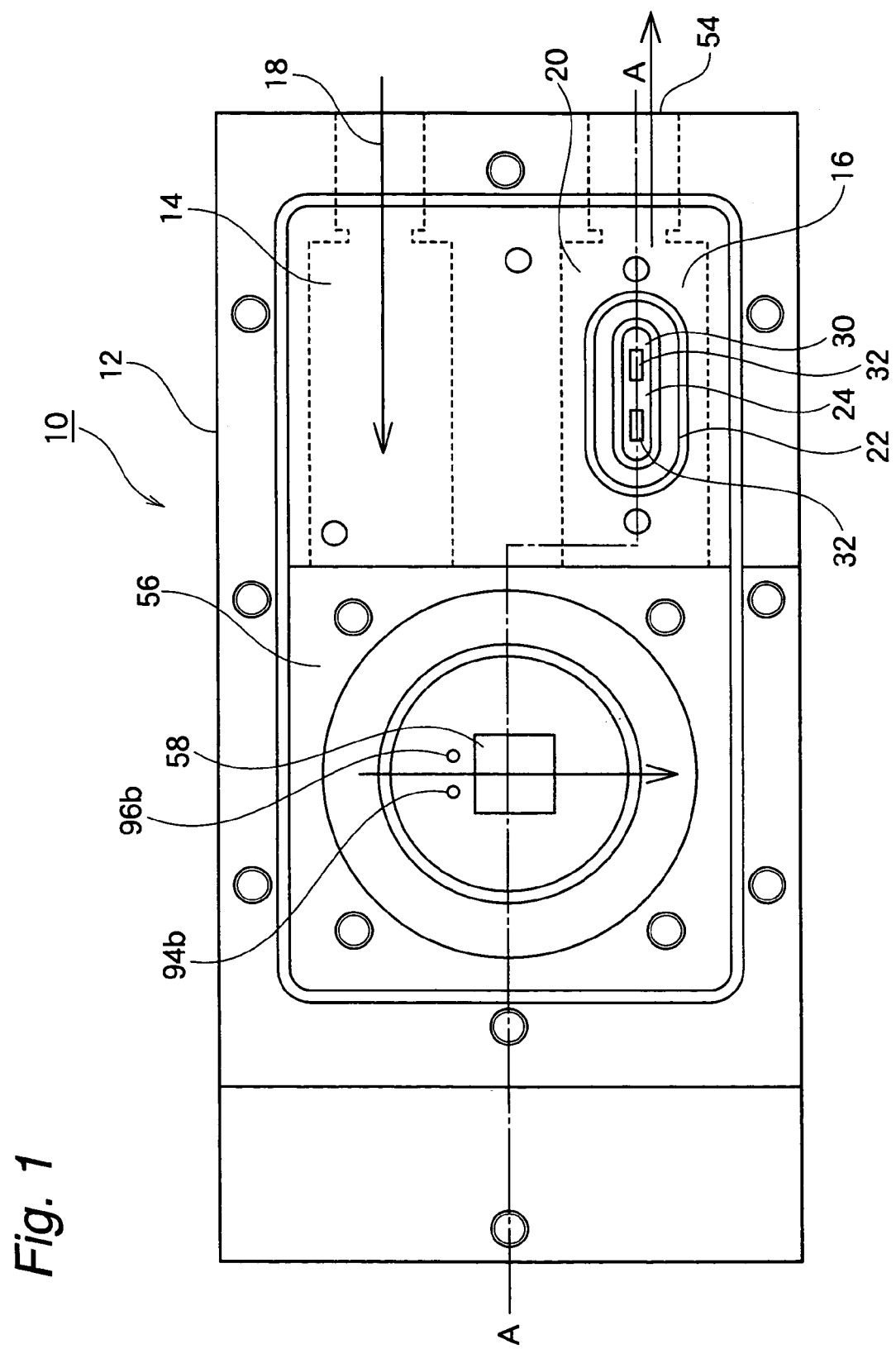
FIG. 1 is a schematic top view showing an example of an apparatus for identifying the liquid type of a gasoline according to the present invention.
Figure 2:
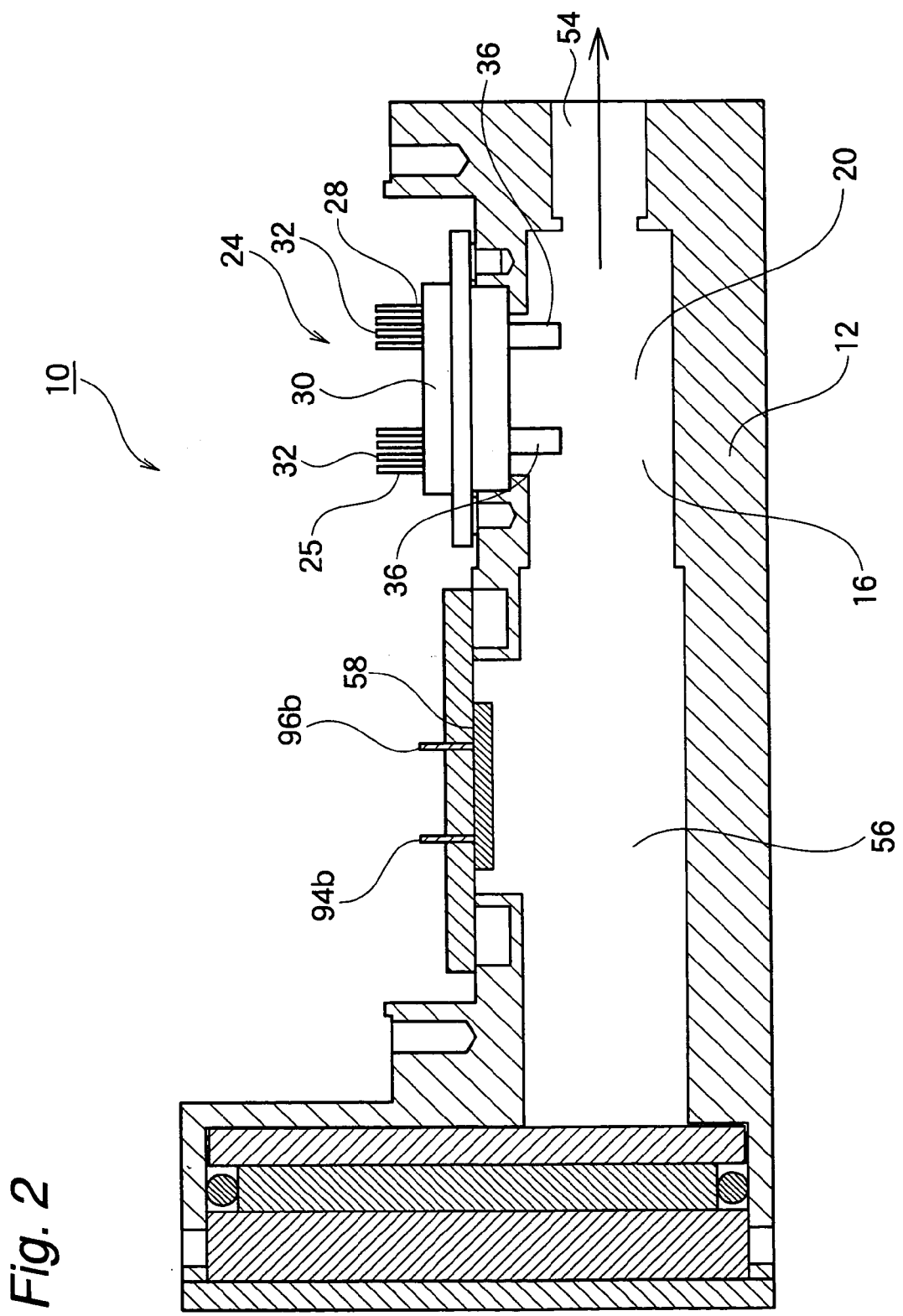
FIG. 2 is a sectional view taken along an A—A line in FIG. 1.
Figure 3:
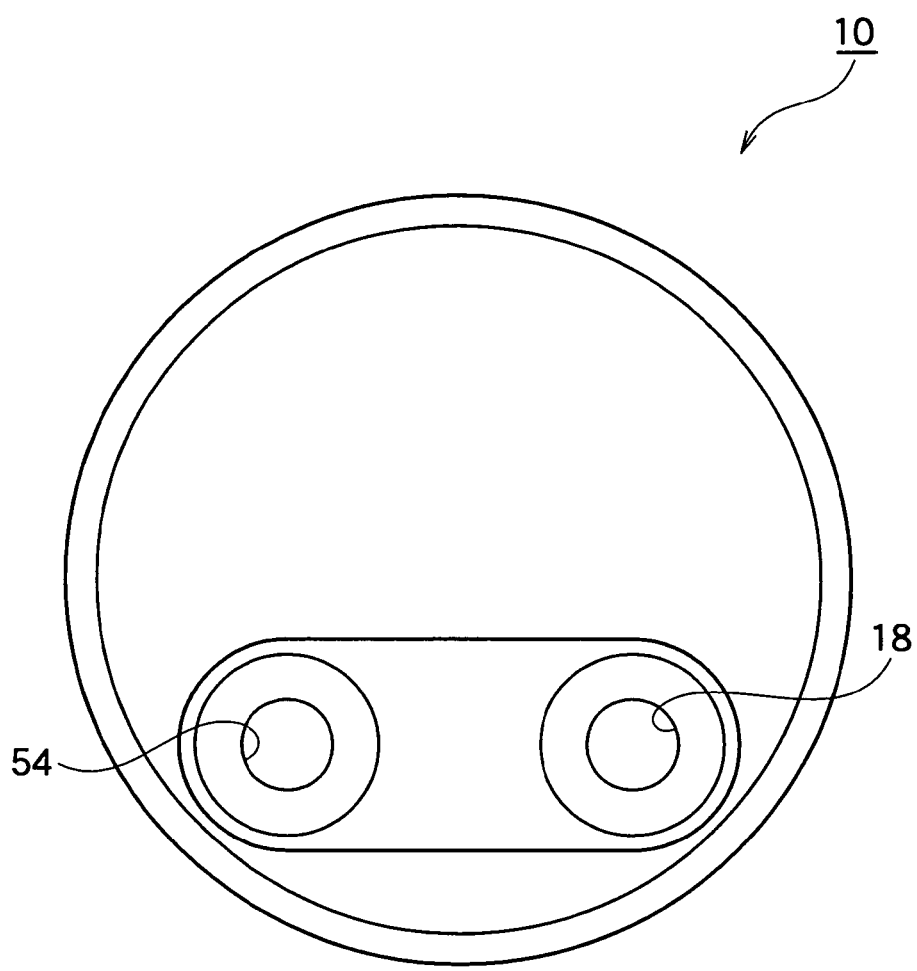
FIG. 3 is a right side view of FIG. 1.
Figure 4:
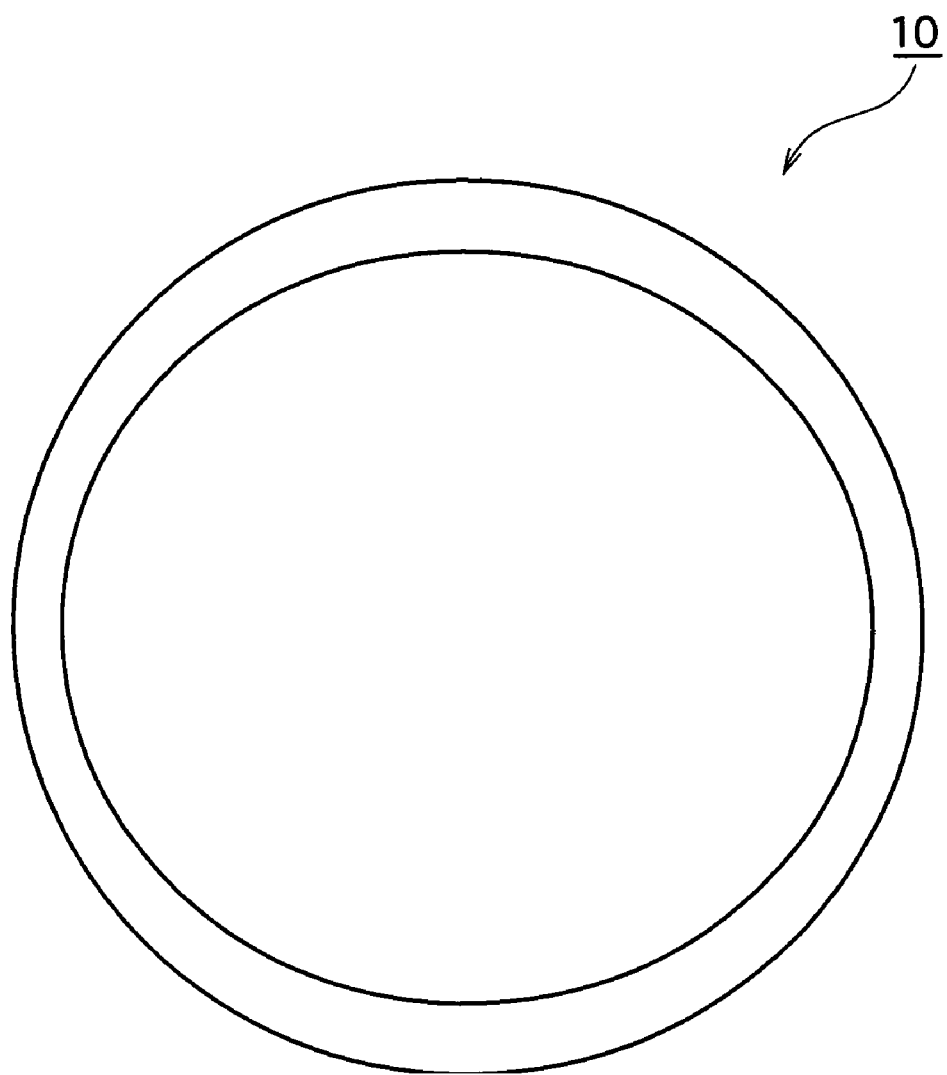
FIG. 4 is a left side view of FIG. 1.
Figure 5:
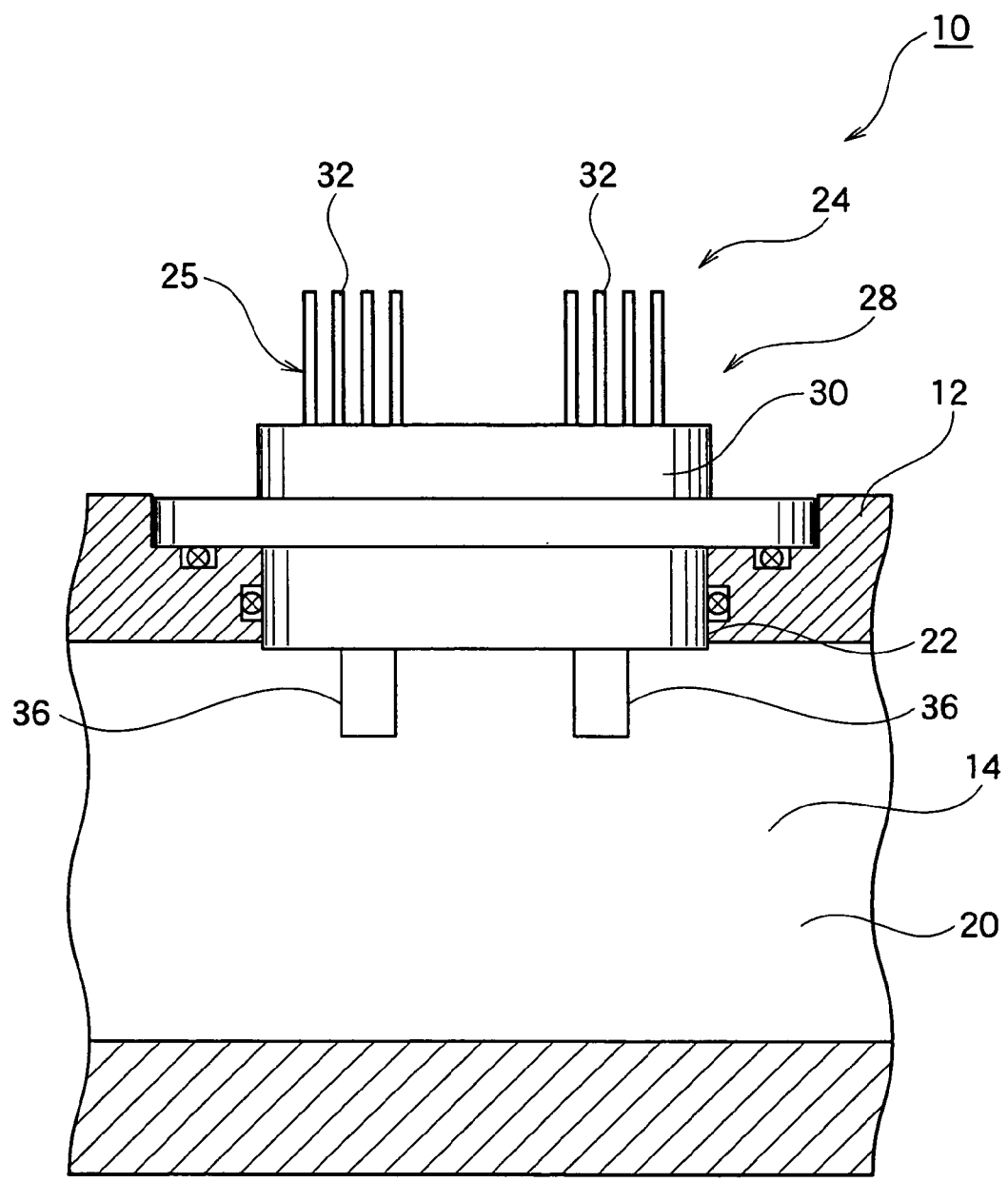
FIG. 5 is a partially enlarged sectional view showing a state in which a liquid type identifying sensor is attached in FIG. 2.
Figure 6:
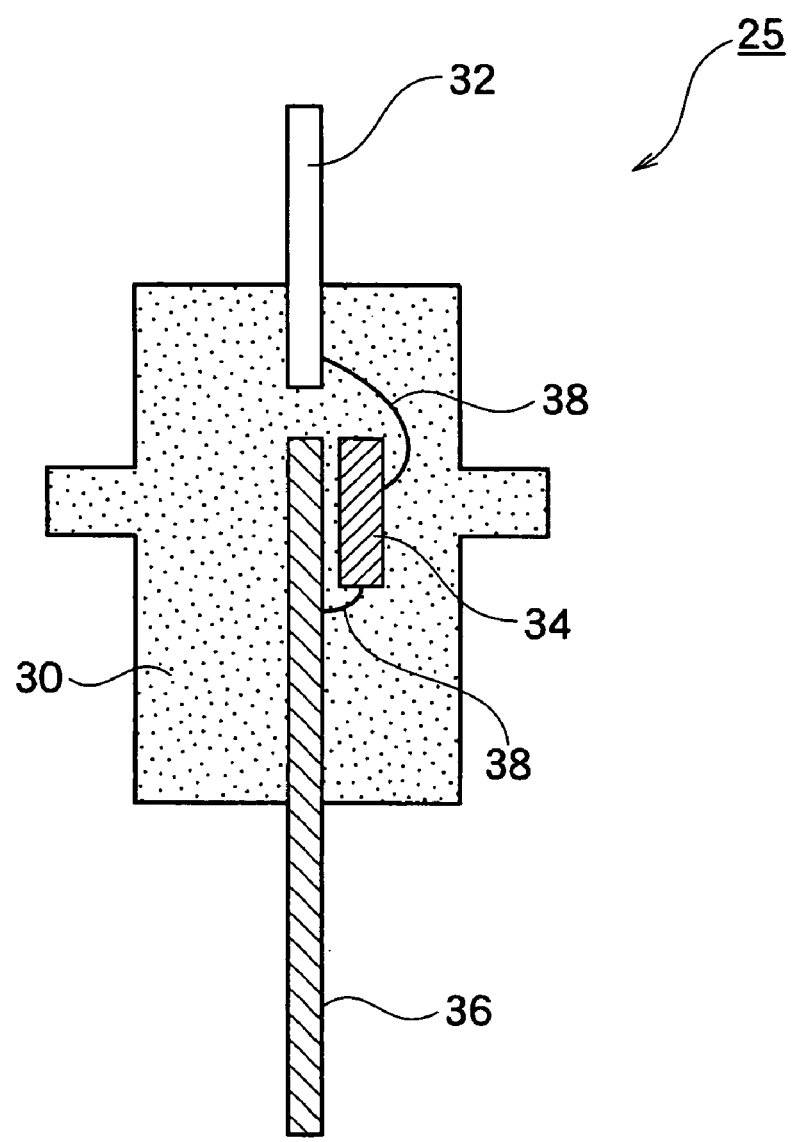
FIG. 6 is a sectional view showing the liquid type identifying sensor.
Figure 7:
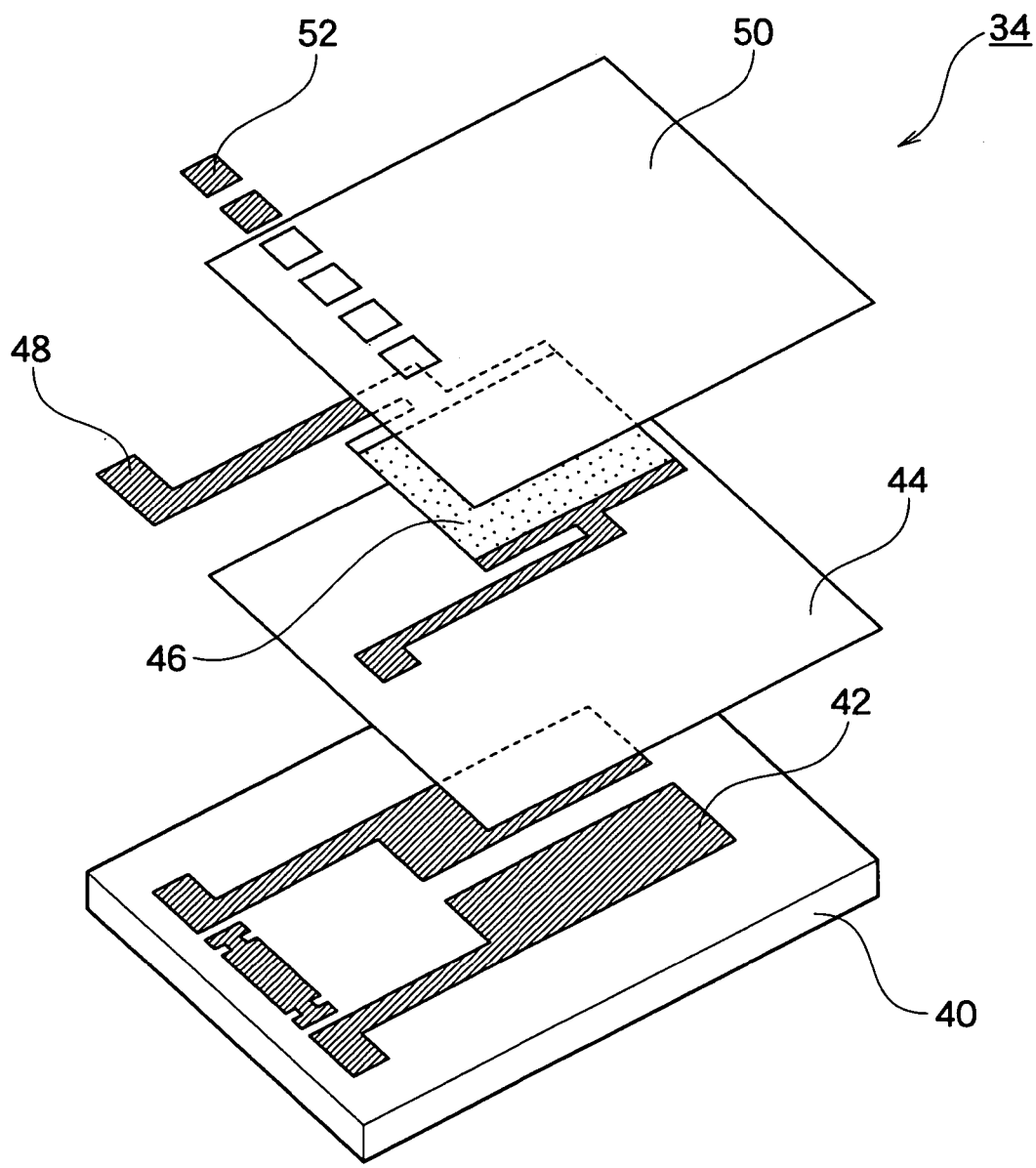
FIG. 7 is a partially enlarged exploded perspective view showing a state in which the thin film chip portions of the liquid type identifying sensor are laminated.
Figure 8:
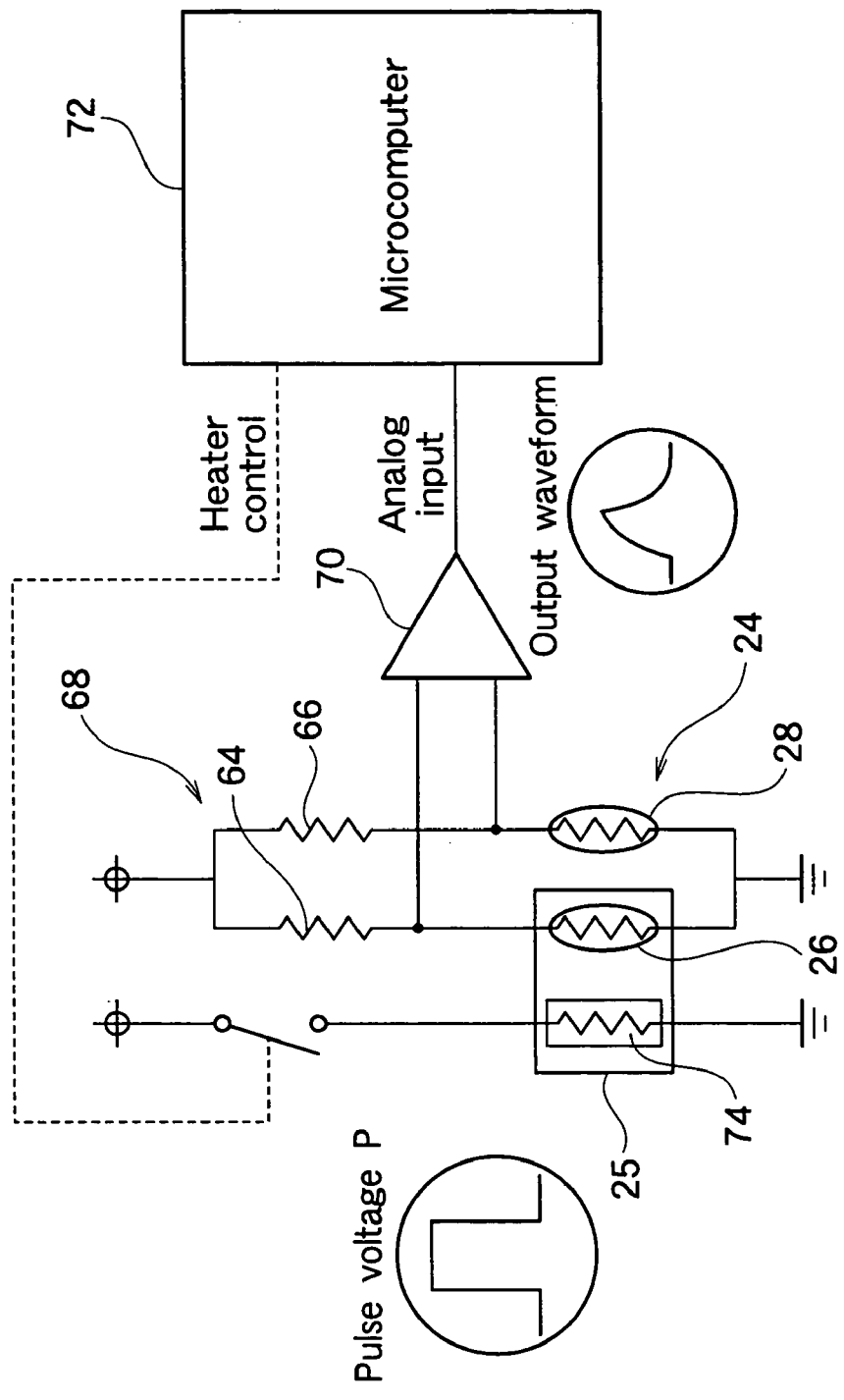
FIG. 8 is a schematic diagram showing the structure of a circuit according to the example of the apparatus for identifying the liquid type of a gasoline according to the present invention.
Figure 9:
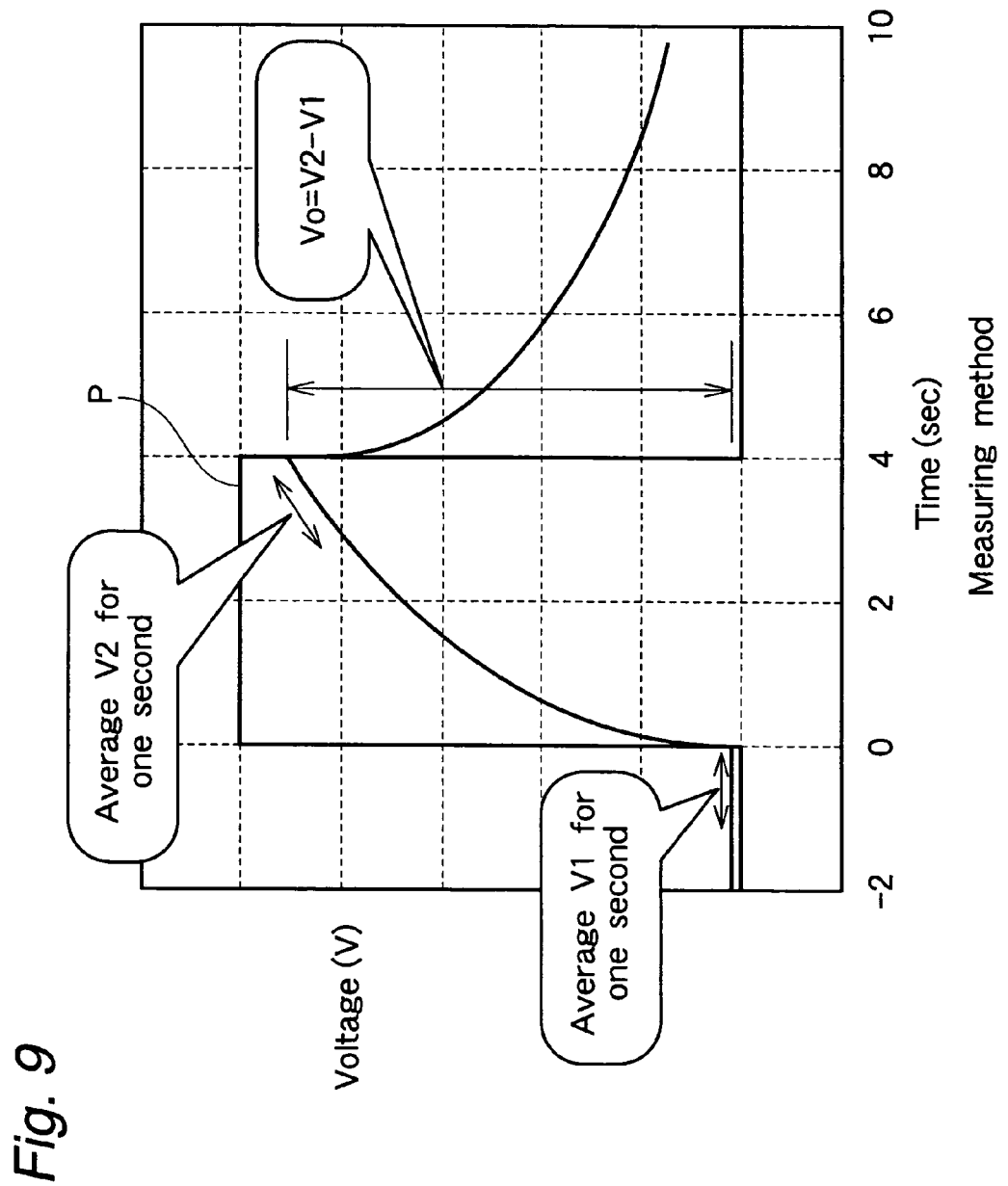
FIG. 9 is a graph showing a relationship between a time and a voltage, illustrating a method for identifying a liquid type using the apparatus for identifying the liquid type of a gasoline according to the present invention.
Figure 10:
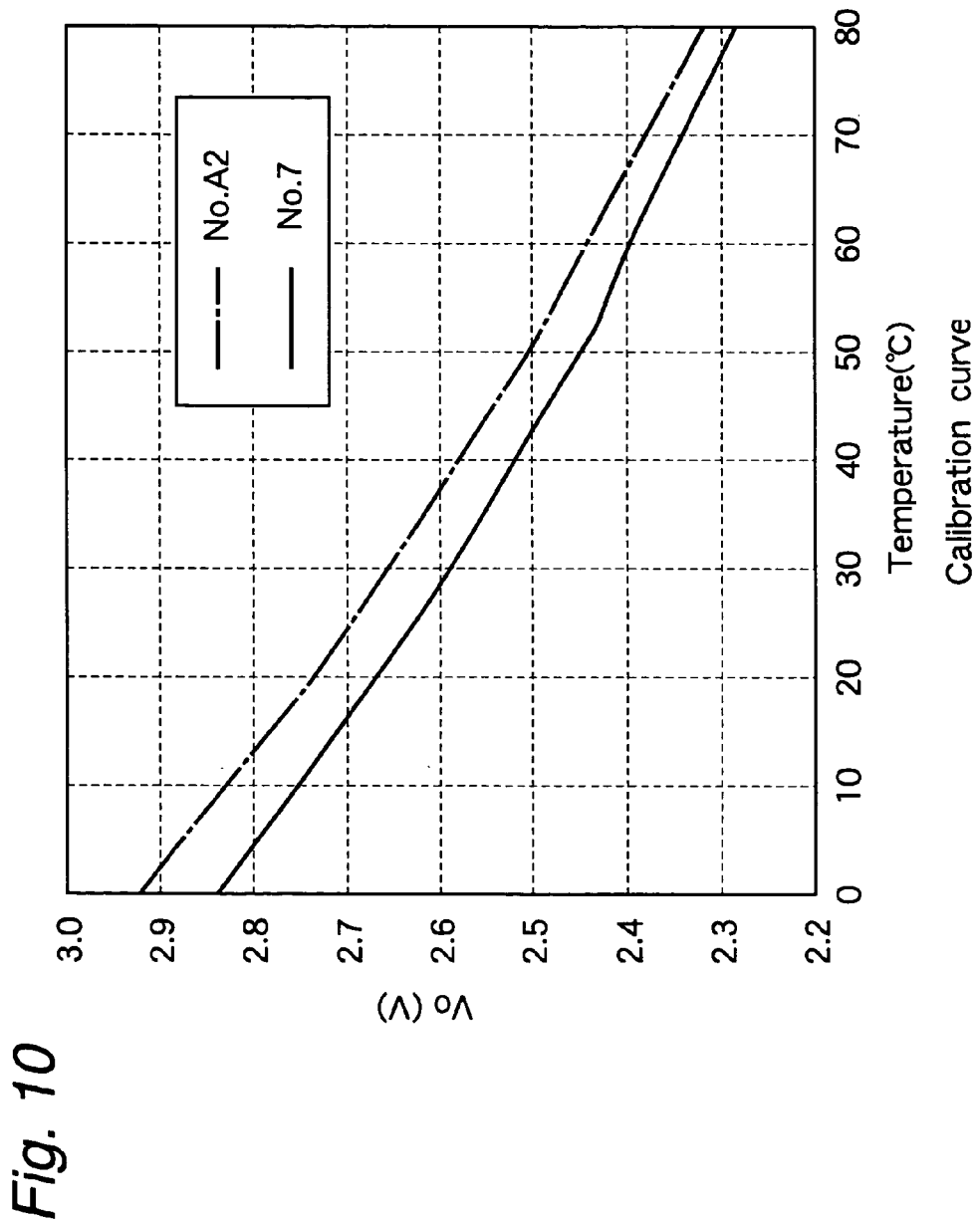
FIG. 10 is a graph showing a calibration curve, illustrating the method for identifying a liquid type using the apparatus for identifying the liquid type of a gasoline according to the present invention.
Figure 11:
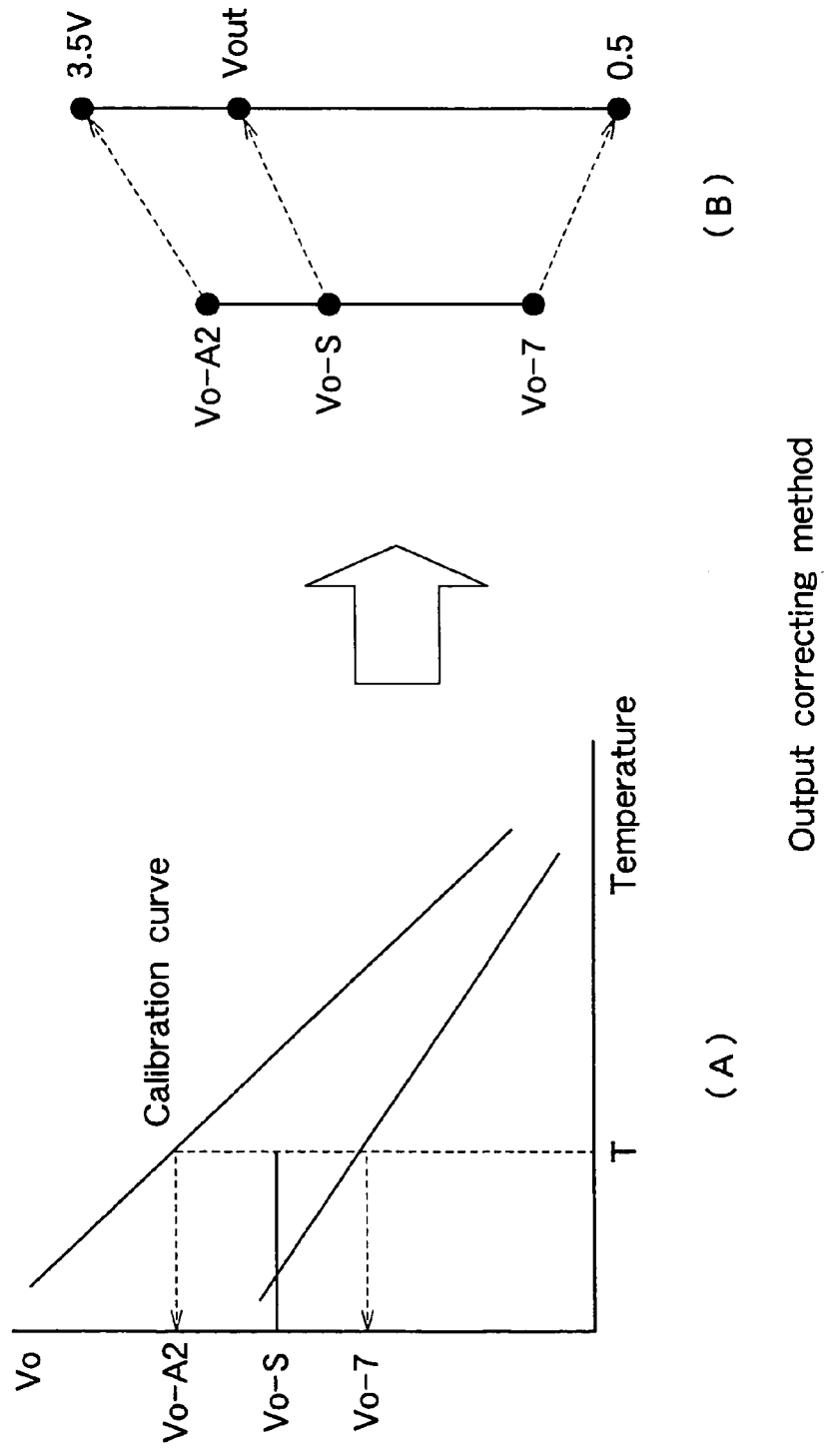
FIG. 11 is a graph showing an output correcting method in the method for identifying a liquid type using the apparatus for identifying the liquid type of a gasoline according to the present invention.

FIG. 1 is a schematic top view showing an example of an apparatus for identifying the liquid type of a gasoline according to the present invention, FIG. 2 is a sectional view taken along an A—A line in FIG. 1, FIG. 3 is a right side view of FIG. 1, FIG. 4 is a left side view of FIG. 1, FIG. 5 is a partially enlarged sectional view showing a state in which a liquid type identifying sensor is attached in FIG. 2, FIG. 6 is a sectional view showing the liquid type identifying sensor, FIG. 7 is a partially enlarged exploded perspective view showing a state in which the thin film chip portions of the liquid type identifying sensor are laminated, FIG. 8 is a schematic diagram showing the structure of a circuit according to the example of the apparatus for identifying the liquid type of a gasoline according to the present invention, FIG. 9 is a graph showing a relationship between a time and a voltage, illustrating a method for identifying a liquid type using the apparatus for identifying the liquid type of a gasoline according to the present invention, FIG. 10 is a graph showing a calibration curve, illustrating the method for identifying a liquid type using the apparatus for identifying the liquid type of a gasoline according to the present invention, and FIG. 11 is a graph showing an output correcting method in the method for identifying a liquid type using the apparatus for identifying the liquid type of a gasoline according to the present invention.

As shown in FIGS. 1 and 2, an apparatus 10 for identifying the liquid type of a gasoline according to the present invention comprises a liquid type identifying apparatus body 12, and a first passage 14 and a second passage 16 which are formed in the liquid type identifying apparatus body 12.

As shown in an arrow of FIG. 1, a gasoline to be identified which flows from a gasoline inlet 18 into the first passage 14 passes through an alcohol content detecting chamber 56. Then, the identified gasoline passes through the alcohol content detecting chamber 56, and thereafter, enters the second passage 16 to temporarily stay in a gasoline liquid type identifying chamber 20. The gasoline liquid type identifying chamber 20 is provided with an opening portion 22 for a liquid type identifying sensor taking the shape of an almost truck in an upper part thereof.

As shown in FIG. 2, a liquid type identifying sensor 24 is attached to the opening portion 22 for the liquid type identifying sensor.

As shown in FIG. 5, the liquid type identifying sensor 24 includes a liquid type identifying sensor heater 25 and a liquid temperature sensor 28 provided apart from the liquid type identifying sensor heater 25 at a constant interval. The liquid type identifying sensor heater 25 and the liquid temperature sensor 28 are formed integrally by a mold resin 30.

As shown in FIG. 6, moreover, the liquid type identifying sensor heater 25 includes a lead electrode 32 and a thin film chip portion 34. Moreover, the liquid type identifying sensor heater 25 is provided with a metallic fin 36 which is protruded into the gasoline liquid type identifying chamber 20 through the opening portion 22 for the liquid type identifying sensor from the mold resin 30 and which comes into direct in contact with the identified gasoline. The lead electrode 32, the thin film chip portion 34 and the fin 36 are mutually connected electrically through a bonding wire 38.

On the other hand, the liquid temperature sensor 28 also has the same structure as that of the liquid type identifying sensor heater 25, and includes the lead electrode 32, the thin film chip portion 34, the fin 36 and the bonding wire 38 respectively.

As shown in FIG. 7, the thin film chip portion 34 is constituted by a thin film-shaped chip in which a substrate 40 formed of $Al_2O_3$, a temperature sensor (temperature detector) 42 formed of PT, an interlayer insulating film 44 formed of $SiO_2$, a heater (heating member) 46 formed of $TaSiO_2$, a heating member electrode 48 formed of Ni, a protective film 50 formed of $SiO_2$, and an electrode pad 52 formed of Ti/Au are provided in order, for example.

While the thin film chip portion 34 of the liquid temperature sensor 28 also has the same structure, it is so constituted as not to cause the heater (heating member) 46 to act but to cause only the temperature sensor (temperature detector) 42 to act.

After the liquid type of the identified gasoline is identified by the liquid type identifying sensor 24, the identified gasoline is discharged from the gasoline liquid type identifying chamber 20 to an outside through a gasoline discharge port 54.

On the other hand, the identified gasoline flowing into the first passage 14 through the gasoline inlet 18 then stays temporarily in the alcohol content detecting chamber 56. In this state, when the gasoline contains the alcohol, the concentration of alcohol is detected by an alcohol detecting sensor 58. Thereafter, the same gasoline is discharged from the alcohol content detecting chamber 56 through the gasoline discharge port 54 of the second passage 16. The details of the detection of the alcohol concentration will be described below.

In FIGS. 1 and 2, moreover, circuit board members connected to the liquid type identifying sensor 24 and the alcohol detecting sensor 58 and lid members for covering them are not shown.

The apparatus 10 for identifying the liquid type of a gasoline according to the present invention has the structure of a circuit shown in FIG. 8.

In FIG. 8, an identifying liquid temperature sensor 26 of the liquid type identifying sensor heater 25 and the liquid temperature sensor 28 in the liquid type identifying sensor 24 are connected to each other through two resistors 64 and 66, thereby constituting a bridge circuit 68. The output of the bridge circuit 68 is connected to the input of an amplifier 70, and the output of the amplifier 70 is connected to the input of a computer 72 constituting an identification control portion.

Moreover, the applied voltage of a heater 74 of the liquid type identifying sensor heater 25 is controlled under the control of the computer 72.

In the apparatus 10 for identifying the liquid type of a gasoline which has such a structure, the liquid type of the gasoline is identified in the following manner.

First of all, the identified gasoline is caused to flow from the gasoline inlet 18 of the first passage 14 of the apparatus 10 for identifying the liquid type of a gasoline and is caused to stay temporarily in the gasoline liquid type identifying chamber 20 of the second passage 16.

As shown in FIGS. 8 and 9, a pulse voltage P is applied to the heater 74 of the liquid type identifying sensor heater 25 under the control of the computer 72 for a predetermined time, that is, four seconds in the present example. Thereafter, a change in the temperature of the analog output of a sensing portion, that is, the sensor bridge circuit 68 shown in FIG. 8 is measured.

More specifically, as shown in FIG. 9, the voltage difference of the sensor bridge circuit 68 is sampled at a predetermined number of times, for example, 256 times in the present example for one second before the pulse voltage P is applied to the heater 74 of the liquid type identifying sensor heater 25. As a result, an average value thereof is set to be an average initial voltage V1. The value of the average initial voltage V1 corresponds to the initial temperature of the identifying liquid temperature sensor 26.

As shown in FIG. 9, the predetermined pulse voltage P, that is, a voltage of 10V in the present example is applied to the heater 74 of the liquid type identifying sensor heater 25 for four seconds. Subsequently, a value obtained by sampling a peak voltage at a predetermined number of times, for example, 256 times in the present example for one second after a predetermined time, for example, 3 seconds in the present example is set to be an average peak voltage V2. The average peak voltage V2 corresponds to the peak temperature of the identifying liquid temperature sensor 26.

A voltage output difference V0 is obtained from a voltage difference between the average initial voltage V1 and the average peak voltage V2, that is, $$V0 = V2 - V1.$$

By such a method, as shown in FIG. 10, calibration curve data to be the correlation of a voltage output difference with a temperature are previously obtained for a predetermined reference gasoline, that is, the heaviest gasoline A2 (which rarely evaporates) and the lightest gasoline No. 7 (which easily evaporates) in the present example. Then, these data are stored in the computer 72 constituting the identification control portion.

Based on the calibration curve data, a proportional calculation is carried out in the computer 72 and the type of the gasoline is identified with the voltage output difference V0 obtained for the identified gasoline.

More specifically, as shown in FIG. 11, a liquid type voltage output Vout for the voltage output difference V0 at a measuring temperature T of the identified gasoline is correlated with an output voltage for a voltage output difference at a measuring temperature for a predetermined threshold reference gasoline (the gasoline A2 and the gasoline No. 7 in the present example) and is thus corrected.

In other words, as shown in FIG. 11(A), a voltage output difference V0-A2 of the gasoline A2, a voltage output difference V0-7 of the gasoline No. 7 and a voltage output difference V0-S of the identified gasoline are obtained at the temperature T based on the calibration curve data.

As shown in FIG. 11(B), the liquid type voltage output Vout of the identified gasoline is obtained by setting the liquid type output of the threshold reference gasoline in this case to have a predetermined voltage, that is, by setting the liquid type output of the gasoline A2 to be 3.5V and the liquid type output of the gasoline No. 7 to be 0.5V in the present example. Thus, a correlation with the characteristics of the gasoline can be acquired.

The liquid type voltage output Vout of the identified gasoline is compared with data previously stored in the computer 72 based on the calibration curve data. Consequently, it is possible to identify the liquid type of the gasoline accurately and rapidly (instantaneously).

The method for identifying the liquid type of a gasoline described above utilizes a natural convection and a principle in which the kinetic viscosity of the gasoline and the sensor output have a correlation.

Figure 15:
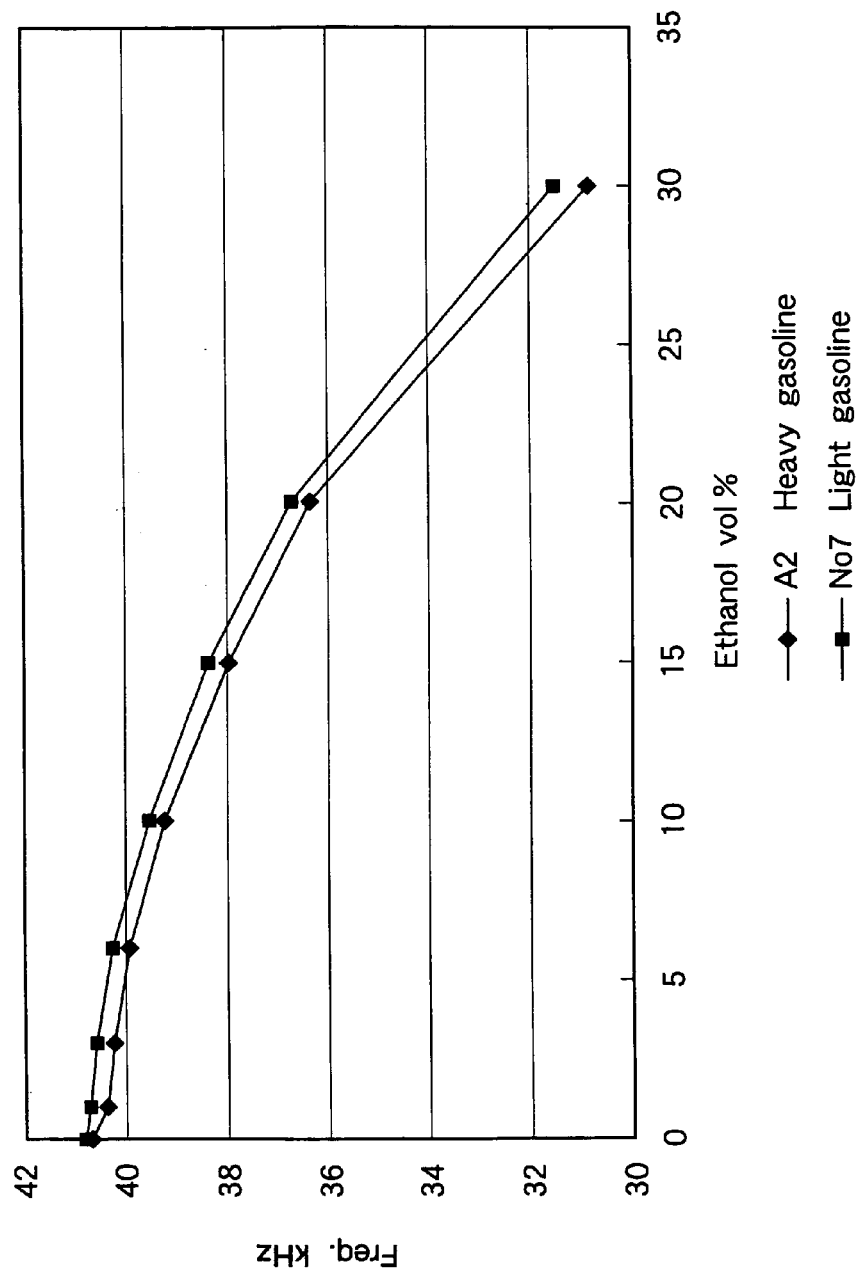
FIG. 15 is a graph showing a relationship between an alcohol concentration and an oscillation frequency.

In such a method for identifying the liquid type of a gasoline, moreover, it is apparent that a greater correlation is obtained with distillation characteristics T30 to T70 of the gasoline shown in FIG. 15, which is desirable.

In the case in which the alcohol is contained in the gasoline in the identification of the liquid type of the gasoline as described above, liquid type identification data are influenced. Consequently, it is hard to identify the liquid type accurately and rapidly.

For this reason, in the present invention, the concentration of the alcohol contained in the gasoline is detected in the following manner.

More specifically, in a state in which the gasoline flowing into the first passage 14 through the gasoline inlet 18 then stays temporarily in the alcohol content detecting chamber 56. In this state, if the alcohol is contained in the gasoline, the concentration of the alcohol content is detected by an alcohol concentration detecting sensor 58 and the gasoline is then discharged from the alcohol content detecting chamber 56 through a gasoline discharge port 54 of the second passage 16.

In the alcohol concentration detecting sensor 58, a difference in an electrostatic capacitance is utilized depending on a difference between the specific inductive capacity of alcohol contained in the gasoline and the specific inductive capacity of the gasoline based on the following Equation 2.

$$C_s = \epsilon_0 (S/D)(\epsilon\, ra(\alpha/100) + \epsilon\, rb(1-\alpha/100)). \qquad \text{Equation 2}$$

Herein, S represents an opposed area of an electrode, D represents a distance between the electrodes, $\epsilon_0$ represents a specific inductive capacity of a vacuum (8.854 E−12F/m), $\epsilon$ ra represents a specific inductive capacity of alcohol, $\epsilon$ rb represents a specific inductive capacity of a gasoline, and $\alpha$ represents an alcohol concentration (%).

Figure 12:
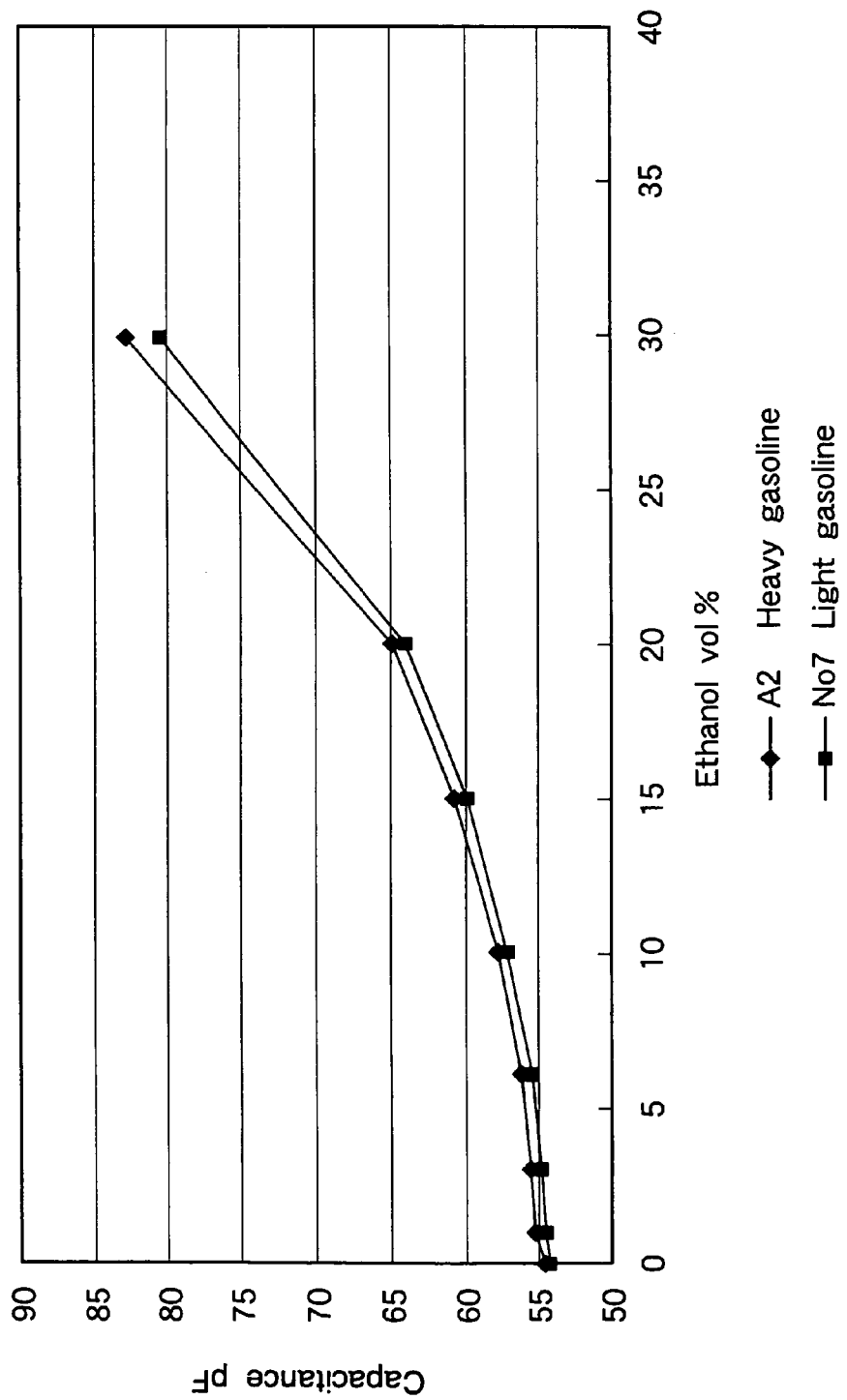
FIG. 12 is a graph showing a relationship between the concentration of alcohol and an electrostatic capacitance.

More specifically, as shown in a graph of FIG. 12 which represents a relationship between an alcohol concentration and an electrostatic capacitance, the alcohol concentration and the electrostatic capacitance have a correlation, and the alcohol concentration is detected by utilizing the correlation.

FIG. 12 shows an example in which ethanol is used for the alcohol and a gasoline is used for the gasoline.

Figure 13:
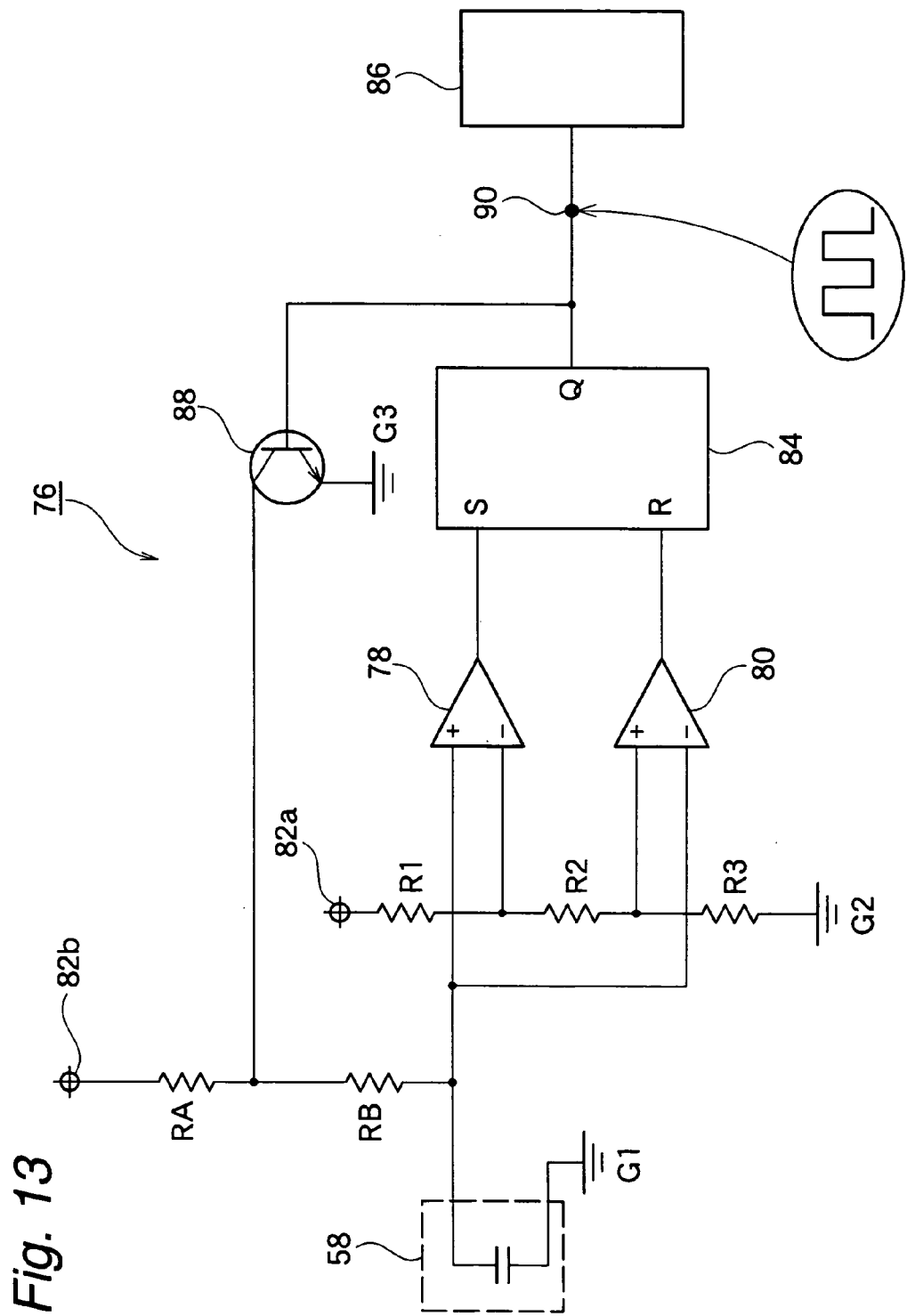
FIG. 13 is a schematic circuit diagram showing the structure of an alcohol concentration detecting device according to the present invention.

Moreover, the alcohol concentration detecting device 10 according to the present invention which uses the alcohol concentration detecting sensor 58 comprises a detecting control portion 76 having a structure shown in a diagram of FIG. 13 illustrating the schematic structure of a circuit.

As shown in FIG. 13, in the detecting control portion 76, one of the electrodes of the alcohol concentration detecting sensor 58 is grounded G1 and the other electrode of the alcohol concentration detecting sensor 58 branches to be connected to the positive and negative inputs of amplifiers (operational amplifiers) 78 and 80.

Moreover, resistors R1 to R3 are connected to a negative 82a of a power supply 82, and furthermore, the negative input of the amplifier 78 is connected between R1 and R2 and the positive input of the amplifier 80 is connected between R2 and R3, and an end of R3 is grounded G2.

The outputs of the amplifiers 78 and 80 are connected to S and R inputs of a flip-flop circuit 84, respectively. The output of the flip-flop circuit 84 is input to the frequency counter of a computer 86.

Furthermore, the wiring of one of the electrodes of the alcohol concentration detecting sensor 58 branches and is connected to a positive 82b of the power supply 82 through resistors RA and RB. A transistor 88 is connected between the resistors RA and RB, and the output of the transistor is connected between the output of the flip-flop circuit 84 and the computer 86. G3 denotes a ground of the transistor 88.

Figure 14:
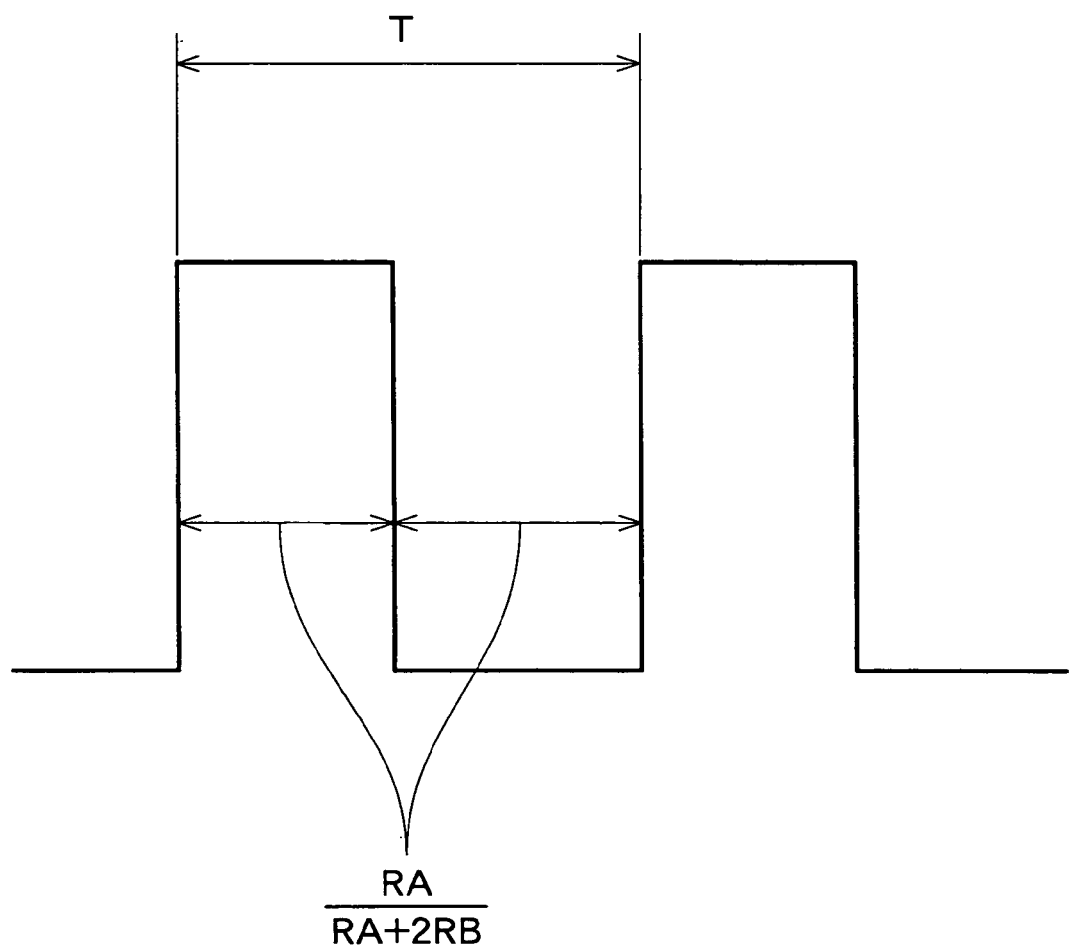
FIG. 14 is a schematic diagram showing a square-wave voltage to be applied by the alcohol concentration detecting device according to the present invention.

In the detecting control portion 76 having such a structure, a square-wave voltage shown in FIGS. 13 and 14 is applied at 90 in FIG. 13.

As is expressed in the following Equation 3, consequently, a relationship between an oscillation frequency f and an electrostatic capacitance $C_s$ is obtained.

$$1/T = f = RA/(RA+2RB) \cdot 1/Cs \ (Hz) \qquad \text{Equation 3}$$

In this case, it is possible to determine an amplitude T by properly setting a duty ratio RA/(RA+2 RB). In the present example, 1.44 was employed for the duty ratio.

From such a relationship, a correlation is taken based on the graph of FIG. 12. As shown in a graph of FIG. 15 representing a relationship between an alcohol concentration and an oscillation frequency, consequently, it is apparent that the alcohol concentration and the oscillation frequency have a correlation. Thus, it is possible to detect the alcohol concentration.

The data in FIGS. 12 and 15 are previously stored in the storage portion of the computer and are compared with data obtained in the detecting control portion 76 so that the alcohol concentration can be detected.

Based on the alcohol concentration detected by the alcohol concentration detecting device, the liquid type identification data in the identification control portion are corrected on the basis of alcohol concentration data which are pre-stored in the identification control portion so that the liquid type is identified.

As is apparent from the Equation 2, in order to obtain the excellent result of a measurement, it is preferable that the distance D between electrodes should be reduced to increase the electrostatic capacitance $C_s$.

In the alcohol concentration detecting device 10 according to the present invention, therefore, the alcohol concentration detecting sensor 58 is constituted in the following manner.

Figure 16:
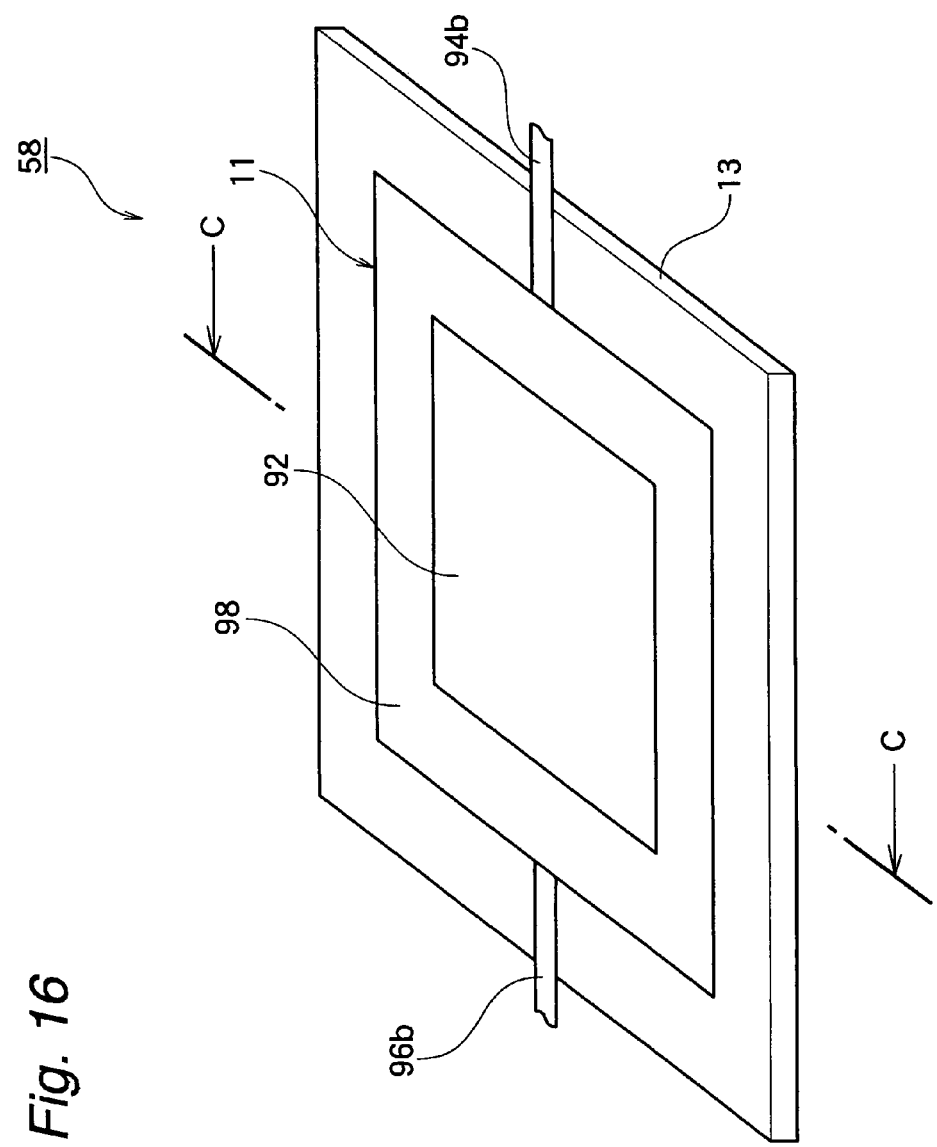
FIG. 16 is a schematic perspective view showing an example of an alcohol concentration detecting sensor in the alcohol concentration detecting device according to the present invention.
Figure 17:
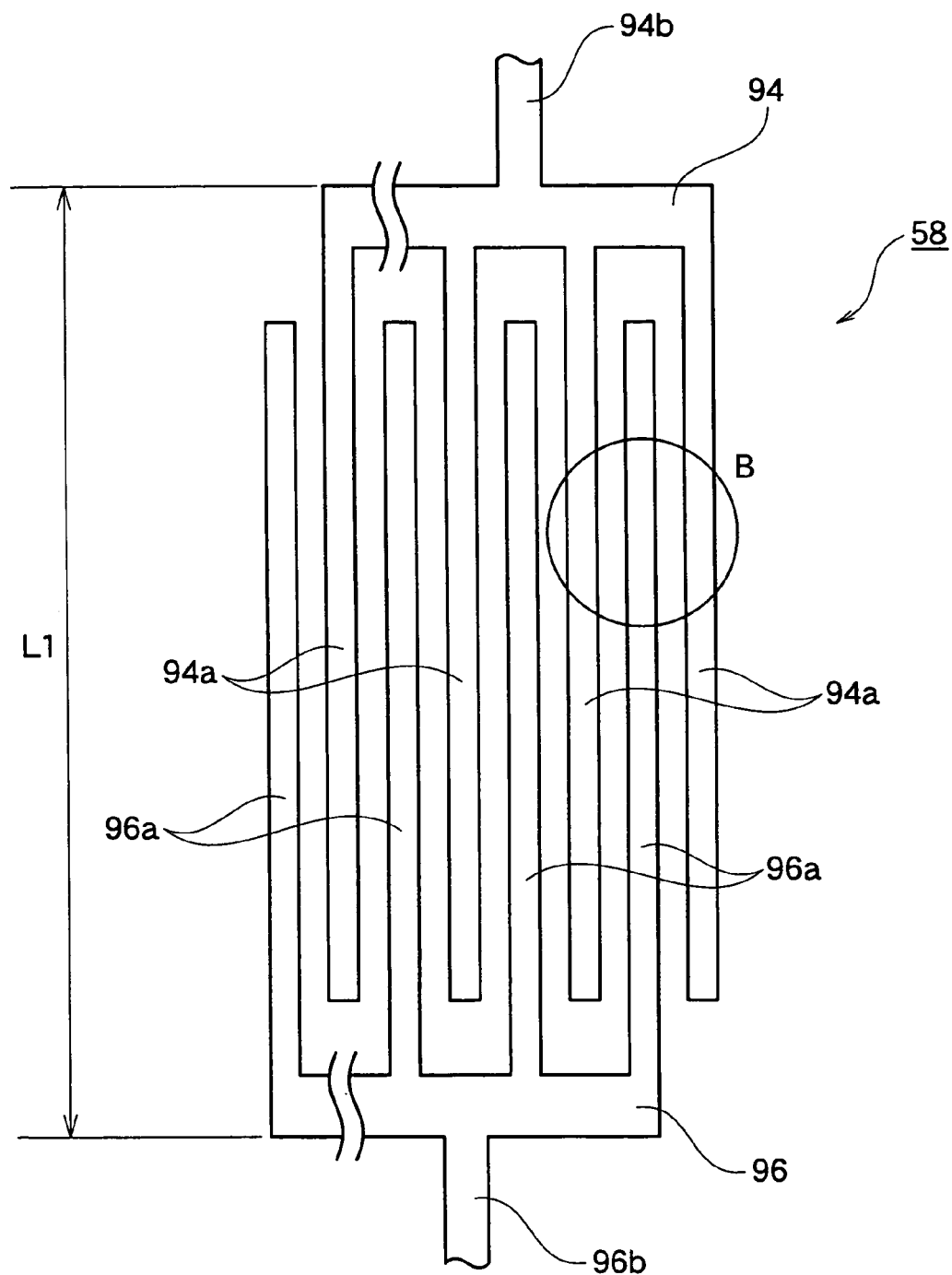
FIG. 17 is a schematic top view showing an electrode wiring pattern in FIG. 16.
Figure 18:
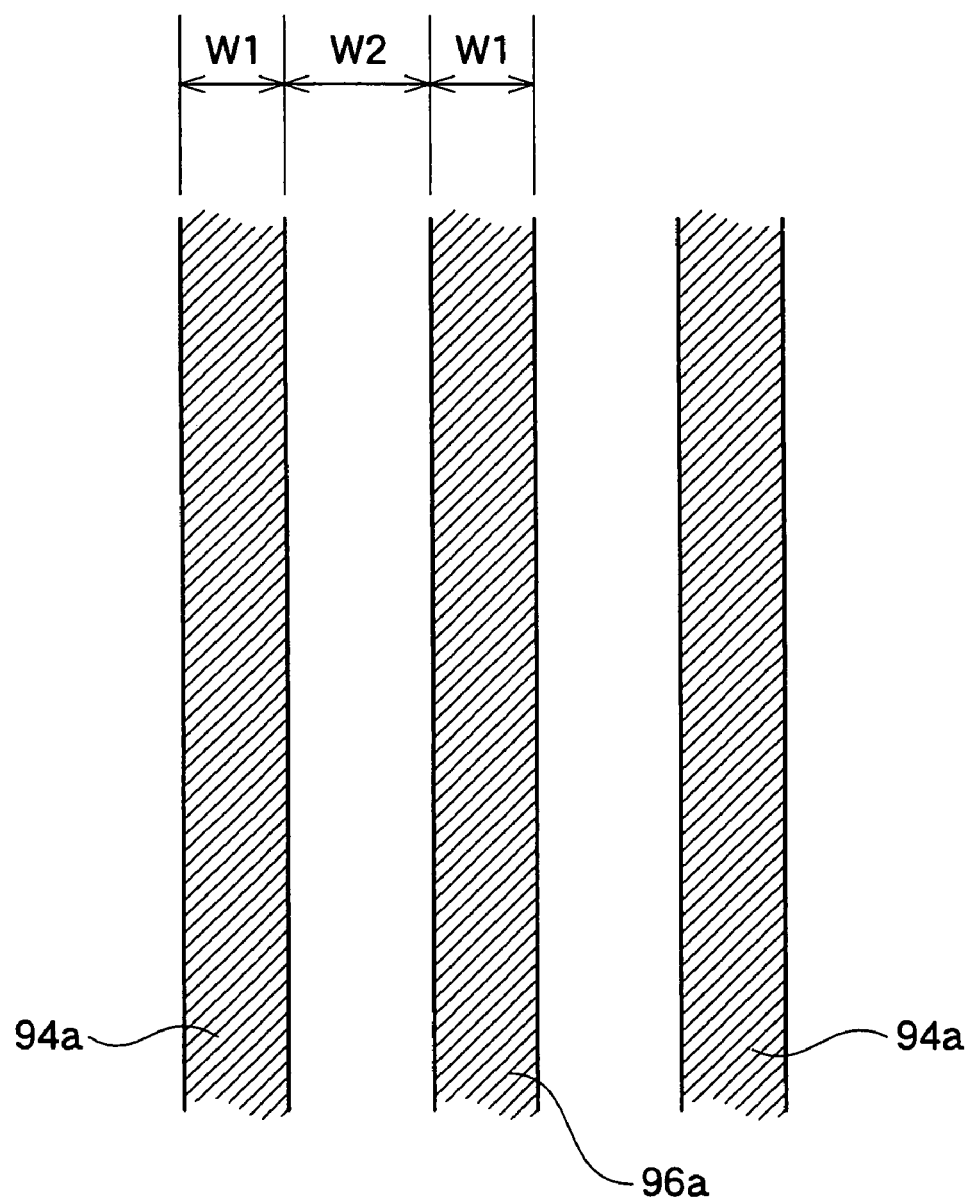
FIG. 18 is an enlarged view showing a B portion in FIG. 17.
Figure 19:
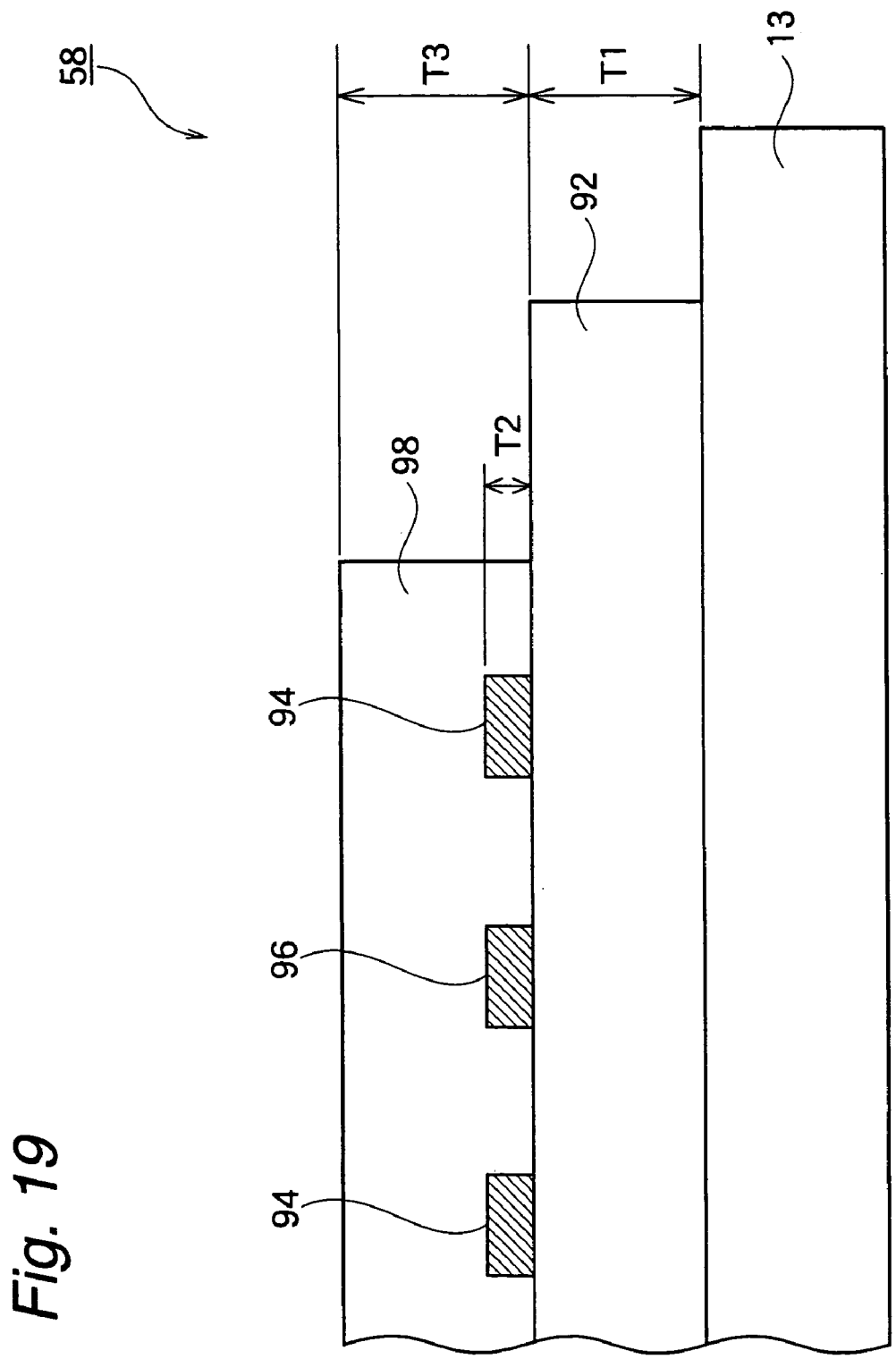
FIG. 19 is a partially enlarged sectional view taken along a C—C line in FIG. 16.

More specifically, FIG. 16 is a schematic perspective view showing an example of the alcohol concentration detecting sensor 58 of the alcohol concentration detecting device according to the present invention, FIG. 17 is a schematic top view showing an electrode wiring pattern in FIG. 16, FIG. 18 is an enlarged view showing a B portion in FIG. 17, and FIG. 19 is a partially enlarged sectional view taken along a C—C line in FIG. 16.

As shown in FIGS. 16 to 19, the alcohol concentration detecting sensor 58 includes an alcohol concentration detecting sensor body 11 constituted by a base material resin film 92, electrode wiring patterns 94 and 96 formed on the base material resin film 92, and an insulating resin 98 covering the surfaces of the electrode wiring patterns 94 and 96. The alcohol concentration detecting sensor body 11 is stuck to a substrate 13 with an adhesive which is not shown.

In this case, it is preferable that a polyimide resin film should be used for the base material resin film 92 in consideration of a flexibility, a chemical resistance and the like. As shown in FIG. 19, moreover, a thickness T1 is not particularly restricted. In the present example, a thickness of 40 μm was used for T1.

Furthermore, the electrode wiring pattern 94 on a positive side and the electrode wiring pattern 96 on a ground (a negative side) have such shapes that positive electrodes 94a and negative electrodes 96a which are comb-toothed are alternately intricate, respectively. In FIG. 16, 94b and 96b denote a fetch electrode portion, respectively.

By such a structure, a plurality of electrodes having a very small distance therebetween can be provided to be compact as a whole.

In this case, while a length L1 of the electrode is not particularly restricted as shown in FIG. 17, it is desirably set to be 100 μm or more in consideration of the electrostatic capacitance of the liquid to be inspected. In the present example, a length of 10 mm was employed for L1.

While a width W1 of each of the positive electrode 94a and the negative electrode 96a is not particularly restricted as shown in FIG. 18, moreover, it is preferably set to be 1 to 50 μm, and more preferably, 5 to 15 μm in consideration of the electrostatic capacitance. Furthermore, a width W2 between the positive electrode 94a and the negative electrode 96a is not particularly restricted but is preferably set to be 1 to 50 μm, and more preferably 5 to 15 μm in consideration of the electrostatic capacitance. In the present example, W1/W2=30/30 μm was employed.

While the numbers of the positive electrodes 94a and the negative electrodes 96a which are comb-toothed are not particularly restricted, moreover, they are preferably equal to or larger than 1, and more preferably, are more increased in consideration of the electrostatic capacitance. In the present example, 64 pairs (128 in total) comb-toothed electrodes were used.

While a thickness T2 of each of the electrode wiring patterns 94 and 96 is not particularly restricted as shown in FIG. 19, furthermore, it is preferably set to be 1 to 50 μm, and more preferably, 5 to 15 μm in consideration of the electrostatic capacitance. In the present example, T2 of 10 μm was employed.

In this case, the electrode wiring patterns 94 and 96 are obtained by selectively etching a conductive metallic foil laminated on one of the surfaces of the base material resin film 92 to form wiring patterns taking predetermined shapes as will be described below.

Although such a conductive metallic foil is not particularly restricted, a copper foil is preferable. Consequently, a high conductivity can be obtained and the concentration of alcohol can be detected very accurately and rapidly.

Furthermore, it is preferable that the insulating resin 98 should be formed by at least one insulating resin selected from an urethane resin, a polyimide resin and an epoxy type resin.

By using such a resin as the insulating resin 98, it is possible to easily apply the insulating resin onto the surfaces of the electrode wiring patterns 94 and 96.

While a thickness T3 of the insulating resin 98 is not particularly restricted as shown in FIG. 19, moreover, it is desirable that the thickness T3 should be smaller with an insulating property and a strength maintained in consideration of the fact that the electrostatic capacitance of the insulating resin itself does not influence sensing. In the present example, T3 of 18 μm was employed.

While the material of the substrate 13 is not particularly restricted, furthermore, it is possible to employ a glass substrate, a ceramics substrate, a resin substrate or the like in consideration of an insulating property. Although the thickness is not particularly restricted, it is preferably set to be 100 to 1000 μm, and more preferably, 250 to 600 μm in consideration of an insulating property, a strength and the like. In the present example, a thickness of 360 μm was employed.

By such a structure, it is possible to reduce the distance between the electrodes by using the electrode wiring patterns 94 and 96 formed on the base material resin film 92. As is apparent from the Equation 2, therefore, the electrostatic capacitance $C_s$ can be increased so that the excellent result of the measurement can be obtained.

In addition, the alcohol concentration detecting sensor 58 is constituted by the base material resin film 92, the electrode wiring patterns 94 and 96 formed on the base material resin film 92, and the insulating resin 98 covering the surfaces of the electrode wiring patterns 94 and 96. For this reason, the sensor itself is flexible, thin, very small and compact, and can be installed everywhere so that the degree of freedom of a design can be enhanced.

Since the surfaces of the electrode wiring patterns 94 and 96 are covered with the insulating resin 98, furthermore, an insulation between the electrodes can be enhanced and is not influenced by a moisture, and shielding can be carried out so as not to be influenced by an electromagnetic wave generated from a body of a car or the like. Furthermore, the alcohol concentration can be measured accurately.

Moreover, the electrode does not directly come in contact with the gasoline. Therefore, a defective operation can be prevented from being caused by a deterioration with the passage of time, foreign matters in the gasoline or the like. Thus, it is possible to detect the alcohol concentration accurately and rapidly.

Figure 20:
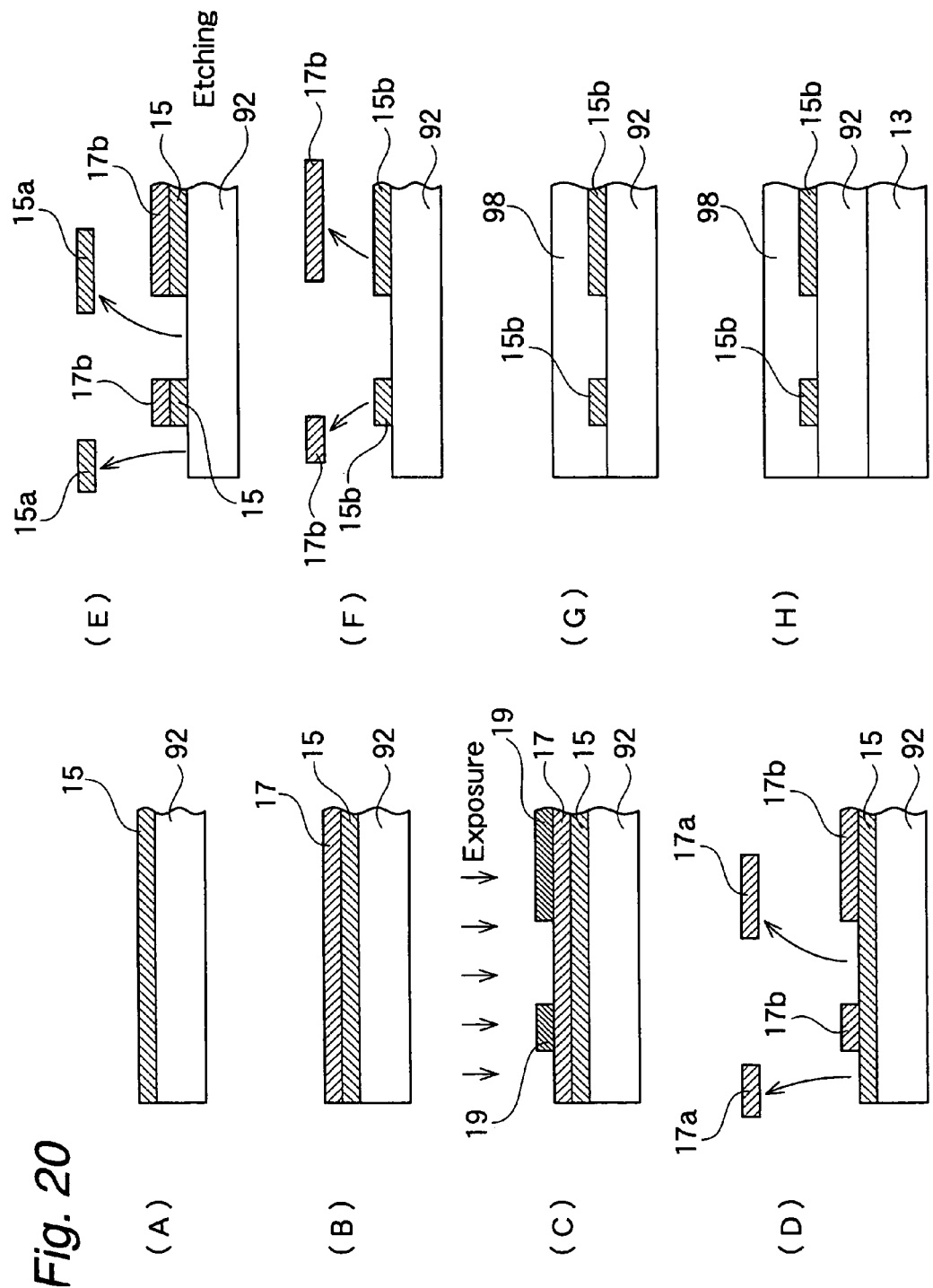
FIG. 20 is a schematic view showing a method for manufacturing the alcohol concentration detecting sensor in the alcohol concentration detecting device according to the present invention.

With reference to FIG. 20, description will be given to a method for manufacturing the alcohol concentration detecting sensor of the alcohol concentration detecting device according to the present invention which has such a structure.

As shown in FIG. 20(A), first of all, a conductive metallic foil 15 is stuck to one of the surfaces of the base material resin film 92 by contact bonding with an adhesive which is not shown (a conductive metallic foil sticking step).

As shown in FIG. 20(B), then, a photoresist 17 is applied onto the whole upper surface of the conductive metallic foil 15 by using a spin coater (3000 rpm), for example (a photoresist applying step).

As shown in FIG. 20(C), next, the photoresist 17 is exposed by ultraviolet rays to take a desirable electrode wiring pattern shape by using a photoresist mask 19 taking a shape corresponding to a predetermined wiring pattern, for example (a photoresist exposing step).

As shown in FIG. 20(D), then, a photoresist portion 17*a* thus exposed is dissolved and removed with a developing solution (a photoresist dissolving and removing step).

As shown in FIG. 20(E), thereafter, a conductive metallic foil portion 15*a* which is not covered with the photoresist 17*b* is subjected to an etching treatment with an etchant such as acid or alkali and is thus removed to obtain a predetermined wiring pattern shape 15*b* (an etching step).

As shown in FIG. 20(F), subsequently, the photoresist 17*b* is dissolved and removed with a dissolving and removing solution such as acetone (a photoresist dissolving and removing step).

As shown in FIG. 20(G), next, the insulating resin 98 is applied onto the surface from which the photoresist is removed by screen printing, for example, and the alcohol concentration detecting sensor body 11 is thus obtained (an insulating resin applying step).

As shown in FIG. 20(H) and FIG. 19, finally, the alcohol concentration detecting sensor body 11 obtained at the insulating resin applying step is stuck onto the substrate 13 (a substrate sticking step).

According to the method for manufacturing the alcohol concentration detecting sensor 58 of the alcohol concentration detecting device in accordance with the present invention, it is possible to obtain an electrode wiring pattern in which a distance between electrodes is very small, for example, approximately 5 μm to 50 μm. Therefore, it is possible to easily supply, on a large scale, an alcohol concentration detecting sensor in which the electrostatic capacitance $C_s$ can be increased and the excellent result of the measurement can be obtained, and furthermore, the sensor itself is thin, very small and compact, and can be installed everywhere so that the degree of freedom of a design can be enhanced.

Figure 21:
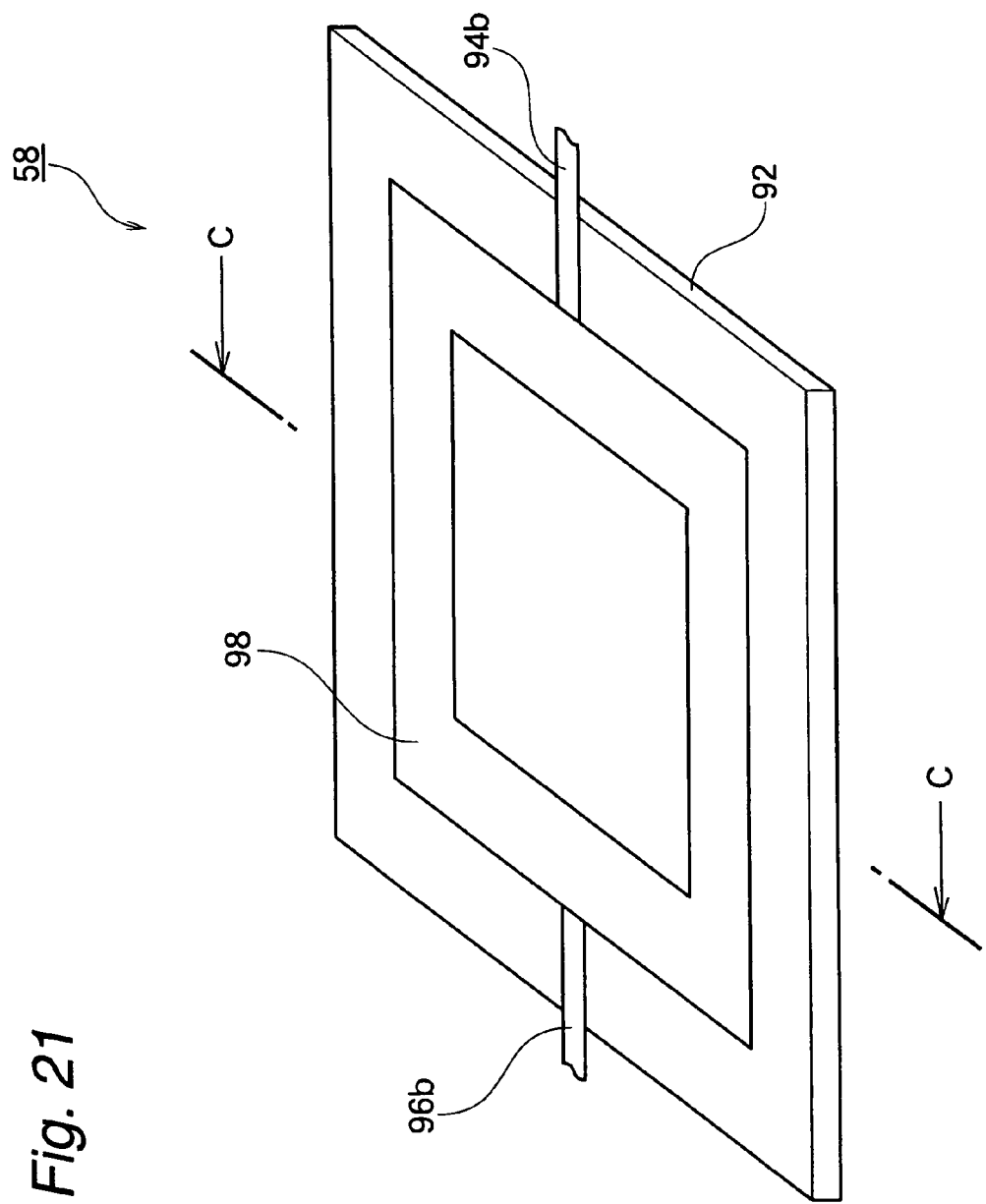
FIG. 21 is a schematic perspective view showing another example of the alcohol concentration detecting sensor in the alcohol concentration detecting device according to the present invention.
Figure 22:
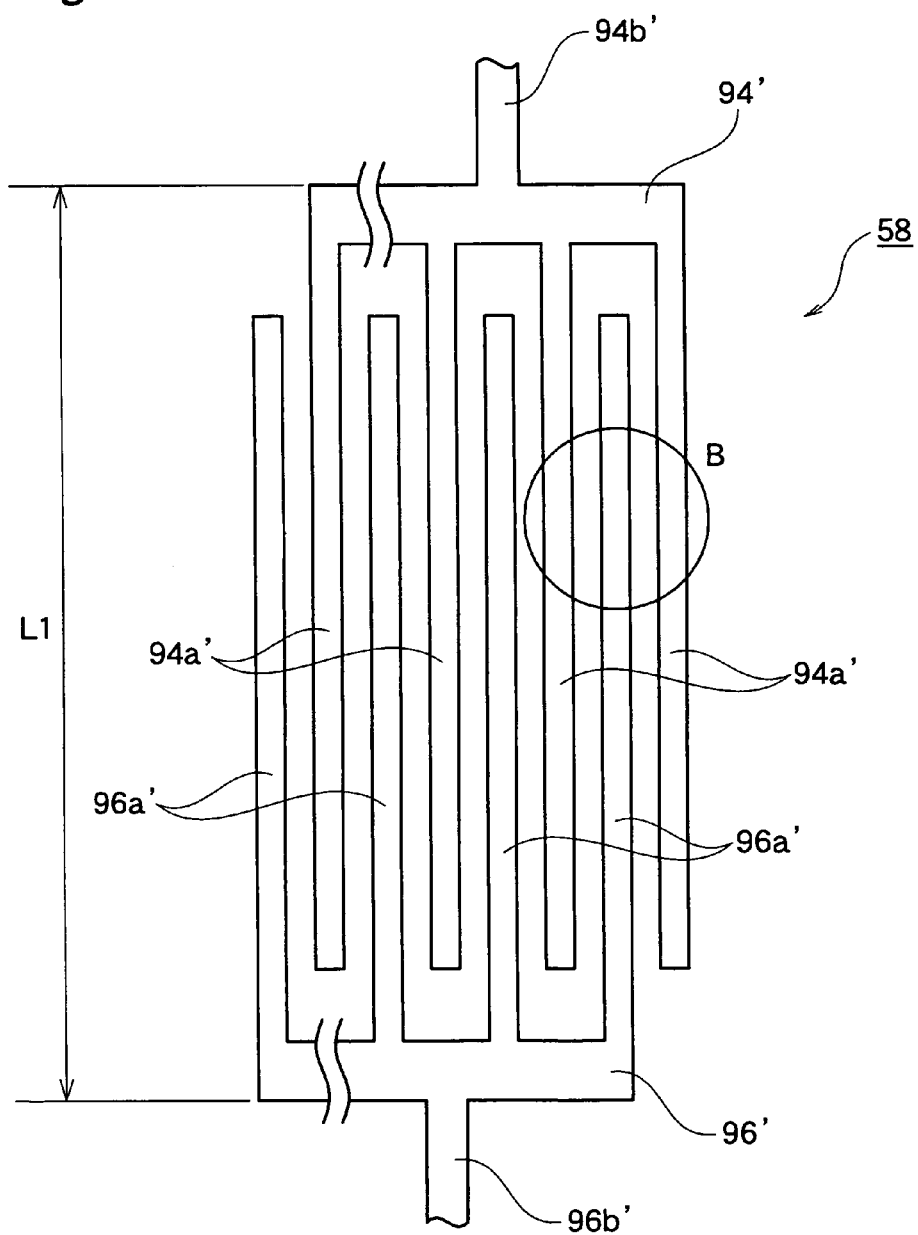
FIG. 22 is a schematic top view showing an electrode wiring pattern in FIG. 21.
Figure 23:
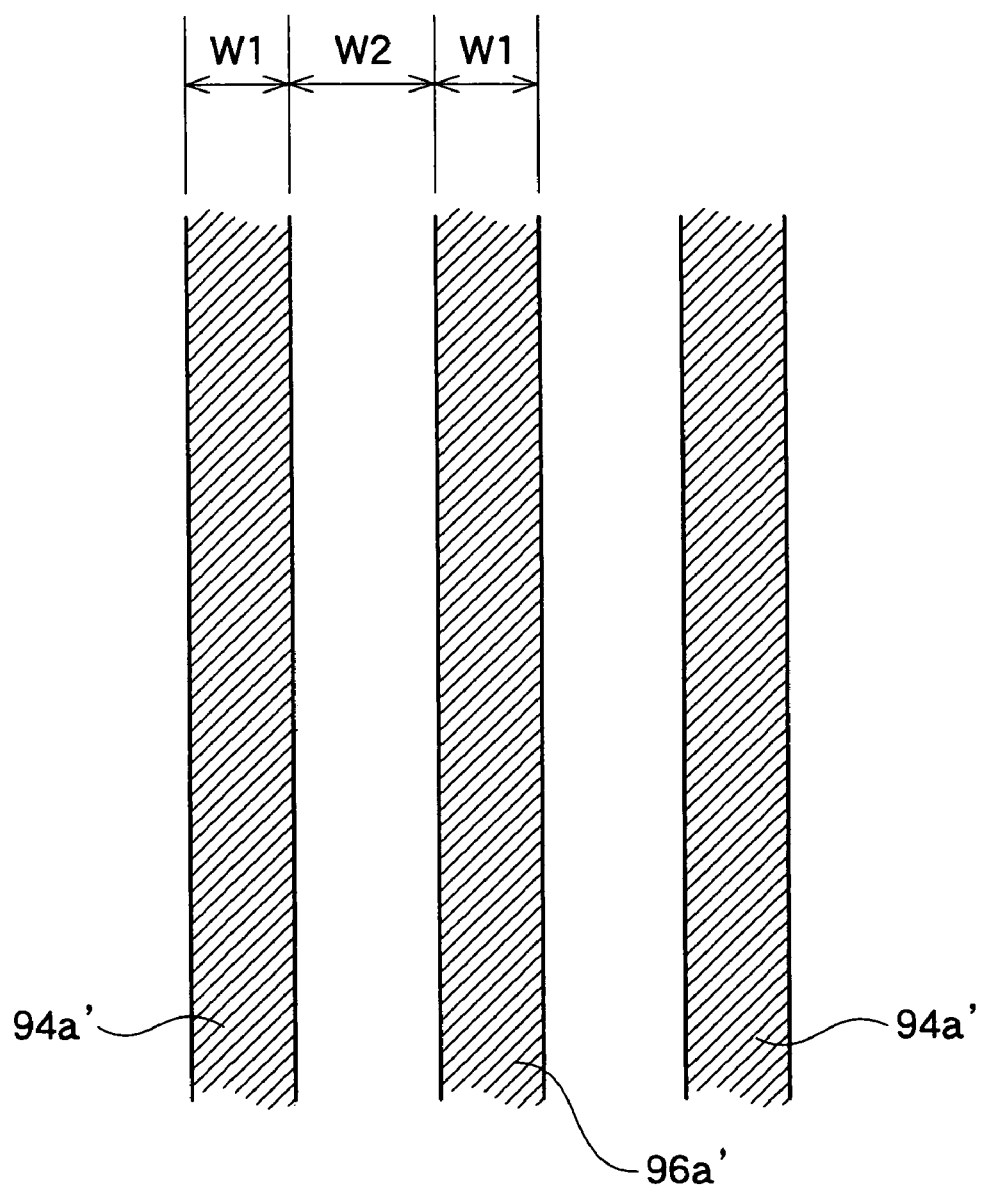
FIG. 23 is an enlarged view showing a B portion in FIG. 22.
Figure 24:
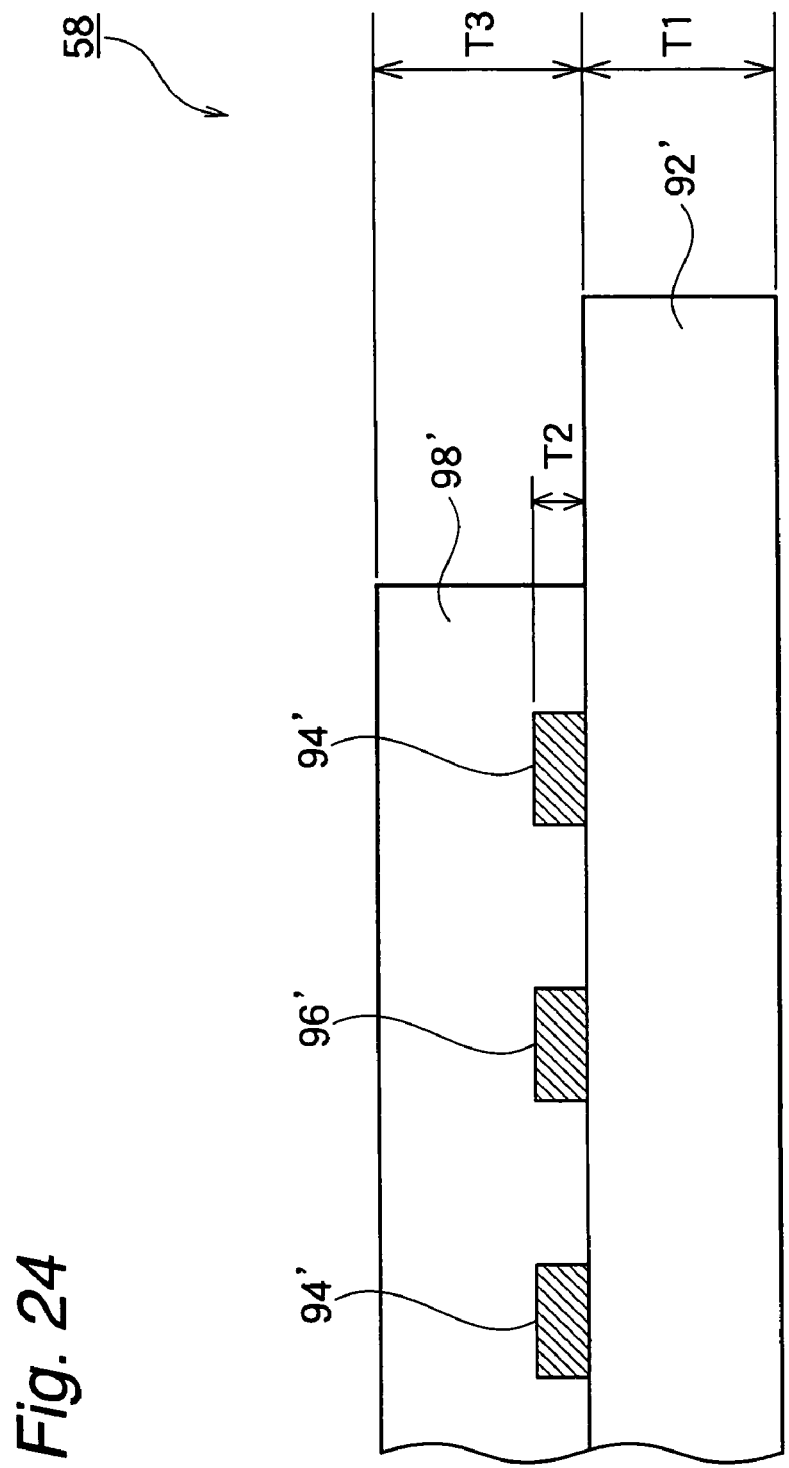
FIG. 24 is a partially enlarged sectional view taken along a C—C line in FIG. 21.

FIG. 21 is a schematic perspective view showing another example of the alcohol concentration detecting sensor 58 of the alcohol concentration detecting device according to the present invention, FIG. 22 is a schematic top view showing an electrode wiring pattern in FIG. 21, FIG. 23 is an enlarged view showing a B portion in FIG. 22, and FIG. 24 is a partially enlarged sectional view taken along a C—C line in FIG. 21.

The alcohol concentration detecting sensor 58 according to the present example has basically the same structure as that of the alcohol concentration detecting sensor 58 according to the example shown in FIGS. 16 to 19. Therefore, the same components are indicated as the reference numerals having a dash and detailed description thereof will be omitted.

The alcohol concentration detecting sensor 58 according to the present example comprises a substrate 92', electrode wiring patterns 94' and 96' formed on the substrate 92', and an insulating coat 98' covering the surfaces of the electrode wiring patterns 94' and 96'.

In this case, the electrode wiring patterns 94' and 96' are obtained by selectively etching a conductive metallic thin film formed on one of the surfaces of the substrate 92' through sputtering to provide a wiring pattern taking a predetermined shape.

While such a conductive metallic thin film is not particularly restricted, nickel, copper, platinum or the like can be used and the platinum is desirably used in consideration of an oxidation resistance or the like.

While a thickness T2 of each of the electrode wiring patterns 94' and 96' is not particularly restricted as shown in FIG. 24, moreover, it is preferably set to be 0.1 to 1.0 µm, and more preferably, 0.1 to 0.5 µm in consideration of an efficiency in the formation of a thin film by the sputtering.

While the material of the substrate 92' is not particularly restricted, furthermore, a glass substrate, a ceramics substrate such as alumina, a resin substrate or the like can be employed in consideration of the fact that the material is not influenced by sputtering or the like. While the thickness is not particularly restricted, it is preferably set to be 100 to 1000 µm, and more preferably, 250 to 600 µm in consideration of an insulating property, a strength or the like. In the present example, a thickness of 360 µm was used. A size depends on the size of a sputtering device, and desirably, 2-inch and 4-inch square sizes can be used.

While the insulating coat 98' is not particularly restricted, moreover, it is preferably constituted by at least one minute insulating coat selected from $SiO_2$, $Al_2O_3$ and the like.

In this case, it is preferable that the insulating coat 98' should be formed by chemical vapor deposition (CVD).

By such a structure, it is possible to obtain, by the chemical vapor deposition (CVD), a very minute and thin insulating coat which is not influenced by a liquid to be inspected such as a gasoline or alcohol, for example, $SiO_2$, $Al_2O_3$ or the like, and the sensor itself can be thin, very small and compact.

While a thickness T3 of the insulating coat 98' is not particularly restricted as shown in FIG. 24, moreover, it is desirable that the thickness T3 should be smaller with an insulating property and a strength maintained in consideration of the fact that the electrostatic capacitance of the insulating coat itself such as an insulating property, a strength and the like does not influence sensing. In the present example, T3 of 1 µm was employed.

By such a structure, it is possible to reduce the distance between the electrodes by using the electrode wiring patterns 94' and 96' formed on the substrate 92'. As is apparent from the Equation 2, therefore, the electrostatic capacitance $C_s$ can be increased and the excellent result of the measurement can be obtained.

In addition, the alcohol concentration detecting sensor is constituted by the substrate 92', the electrode wiring patterns 94' and 96' formed on the substrate 92', and the insulating coat 98' covering the surfaces of the electrode wiring patterns 94' and 96'. For this reason, the sensor itself is thin, very small and compact, and can be installed everywhere so that the degree of freedom of a design can be enhanced.

Since the surfaces of the electrode wiring patterns are covered with the insulating coat 98', furthermore, an insulation between the electrodes can be enhanced and is not influenced by a moisture, and shielding can be carried out so as not to be influenced by an electromagnetic wave generated from a body of a car or the like, and furthermore, the alcohol concentration can be measured accurately.

Moreover, the electrode does not directly come in contact with the gasoline. Therefore, a defective operation can be prevented from being caused by a deterioration with the passage of time, foreign matters in the gasoline or the like. Thus, it is possible to detect the alcohol concentration accurately and rapidly.

In addition, the substrate 92' is provided. Therefore, it is easy to assemble and attach the alcohol concentration detecting sensor into the apparatus.

Furthermore, it is possible to obtain an electrode wiring pattern having a thickness of 0.1 to 5 µm by sputtering at a very small distance between the electrodes, for example, within a range of approximately 5 µm to 50 µm by the sputtering. Therefore, the electrostatic capacitance $C_s$ can be increased so that the excellent result of the measurement can be obtained.

Figure 25:
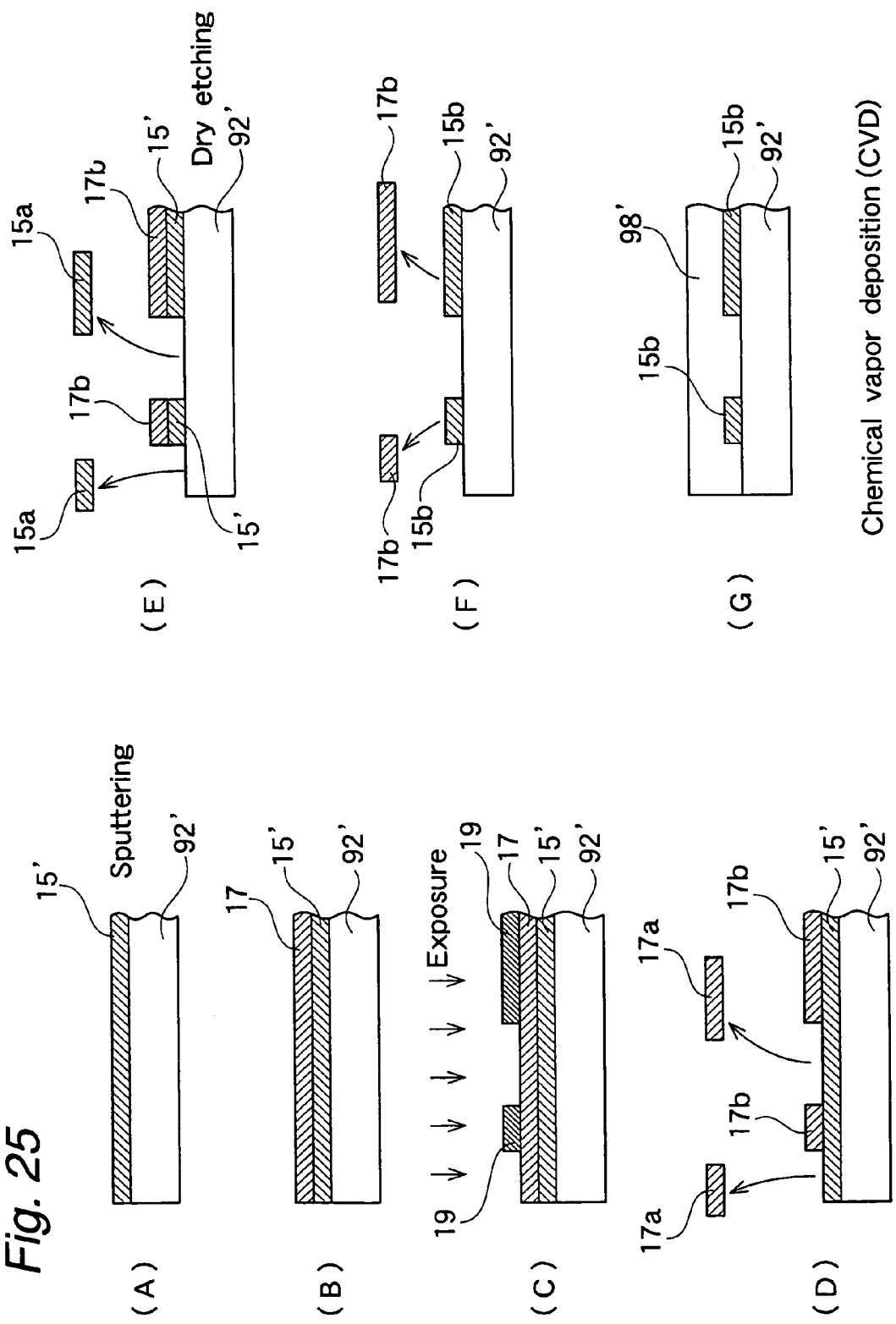
FIG. 25 is a schematic view showing a method for manufacturing the alcohol concentration detecting sensor in the alcohol concentration detecting device according to the present invention.

With reference to FIG. 25, description will be given to a method for manufacturing the alcohol concentration detecting sensor of the alcohol concentration detecting device according to the present invention which has such a structure.

As shown in FIG. 25(A), first of all, a conductive metallic thin film 15' is formed on one of the surfaces of the substrate 92' by the sputtering (a conductive metallic thin film forming step).

As shown in FIG. 25(B), then, a photoresist 17 is applied onto the whole upper surface of the conductive metallic thin film 15' by using a spin coater (3000 rpm), for example (a photoresist applying step).

As shown in FIG. 25(C), next, the photoresist 17 is exposed by ultraviolet rays to take a desirable electrode wiring pattern shape by using a photoresist mask 19 taking a shape corresponding to a predetermined wiring pattern, for example (a photoresist exposing step).

As shown in FIG. 25(D), then, a photoresist portion 17a thus exposed is dissolved and removed with a developing solution (a photoresist dissolving and removing step).

As shown in FIG. 25(E), thereafter, a conductive metallic thin film portion 15a which is not covered with the photoresist 17b is subjected to a dry etching treatment by using an argon ion or the like, for example, and is thus removed to obtain a predetermined wiring pattern shape 15b (an etching step).

As shown in FIG. 25(F), subsequently, the photoresist 17b is dissolved and removed with a dissolving and removing solution such as acetone (a photoresist dissolving and removing step).

As shown in FIG. 25(G), finally, the insulating coat 98' is formed, by the chemical vapor deposition (CVD), on the surface from which the photoresist is removed (an insulating coat forming step).

By such a structure, it is possible to obtain an electrode wiring pattern having a thickness of 0.1 to 5 µm by the sputtering at a very small distance between the electrodes, for example, within a range of approximately 5 µm to 50 µm. Therefore, it is possible to easily supply, on a large scale, an alcohol concentration detecting sensor in which the electrostatic capacitance CS can be increased so that the excellent result of the measurement can be obtained, and furthermore, the sensor itself is thin, very small and compact, and can be installed everywhere so that the degree of freedom of a design can be increased.

Figure 26:
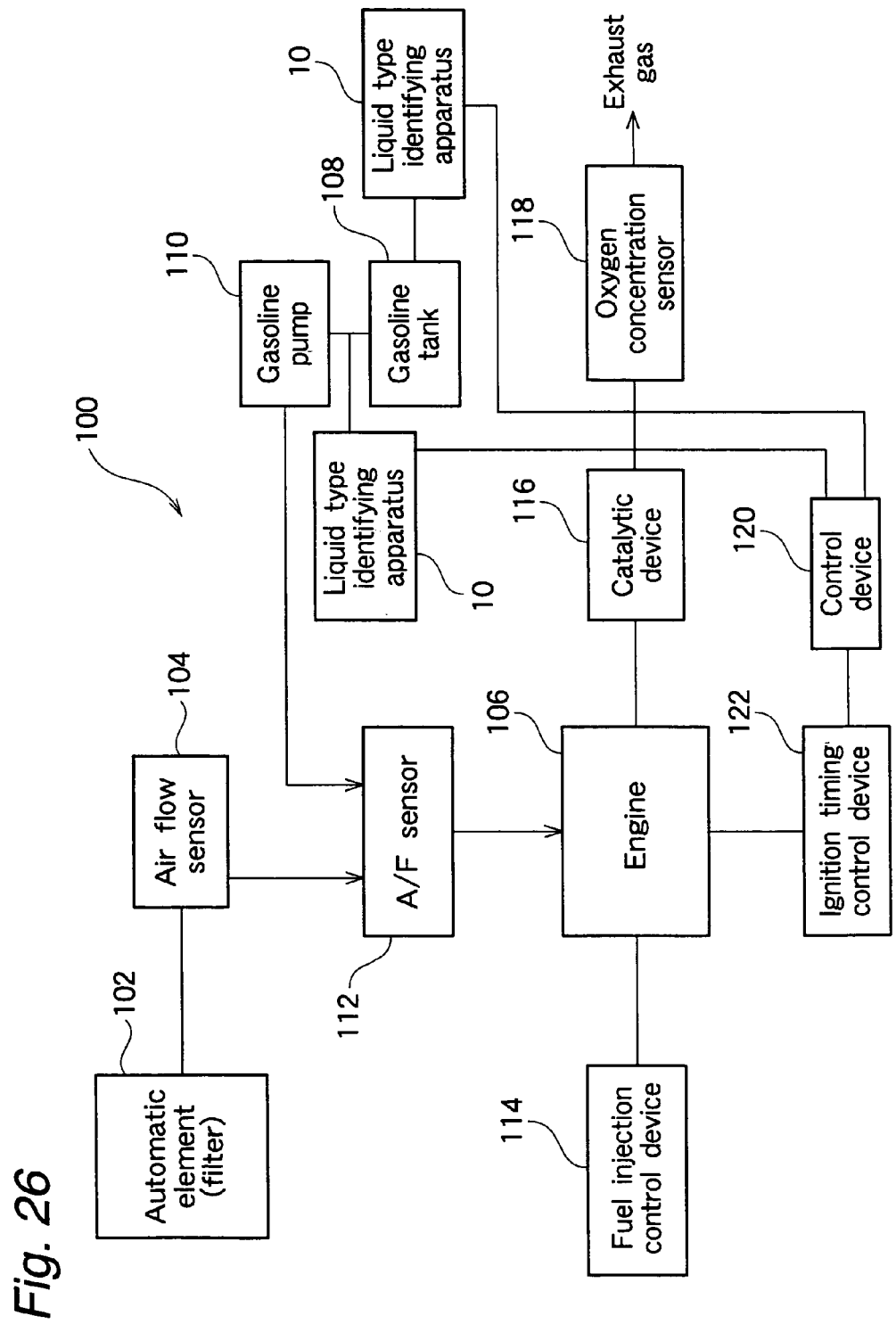
FIG. 26 is the same schematic diagram as FIG. 28, illustrating an example in which an apparatus 10 for identifying the liquid type of a gasoline according to the present invention is applied to a car system.
Figure 28:
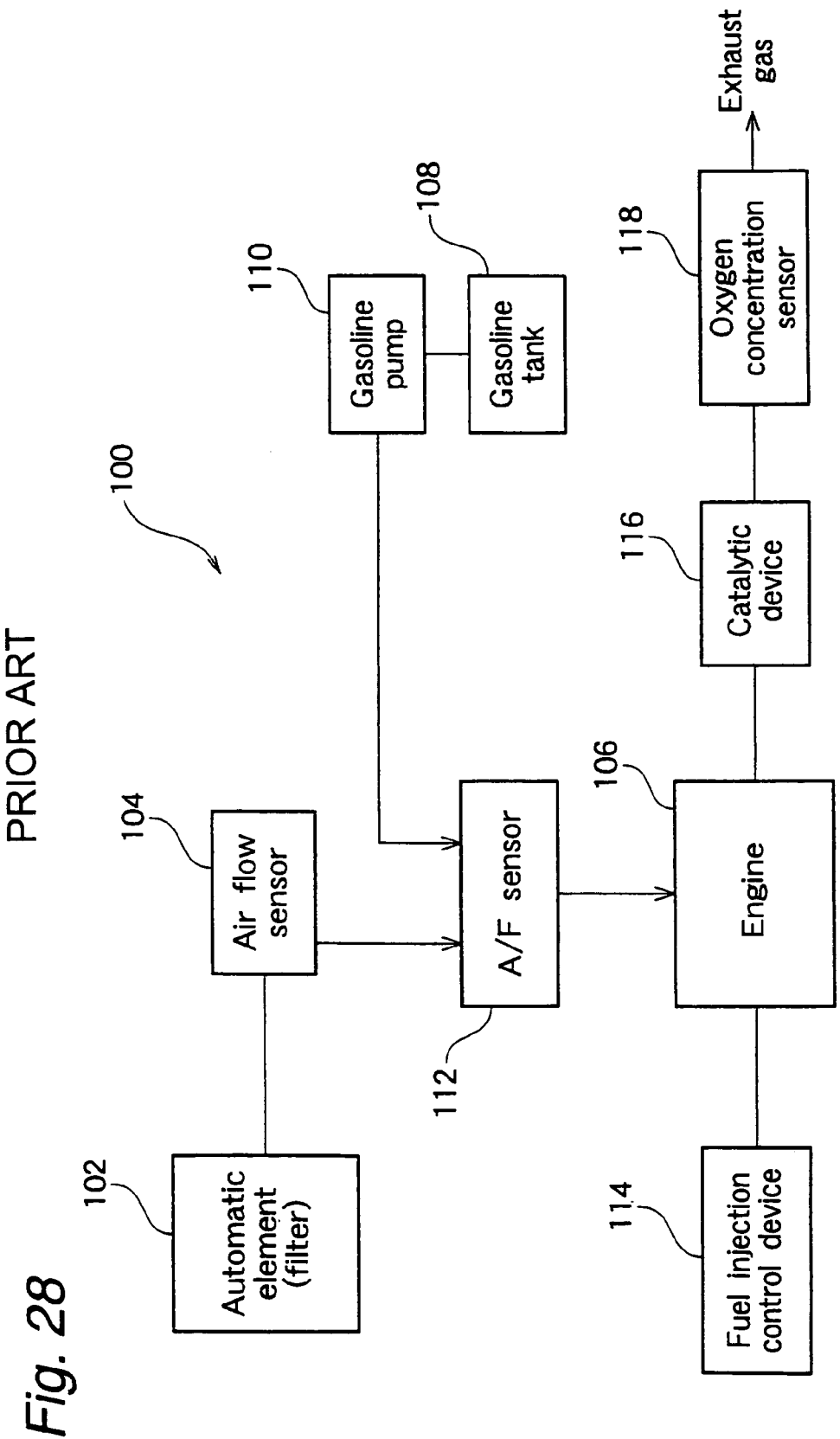
FIG. 28 is a schematic diagram showing a conventional car system.
Figure 29:
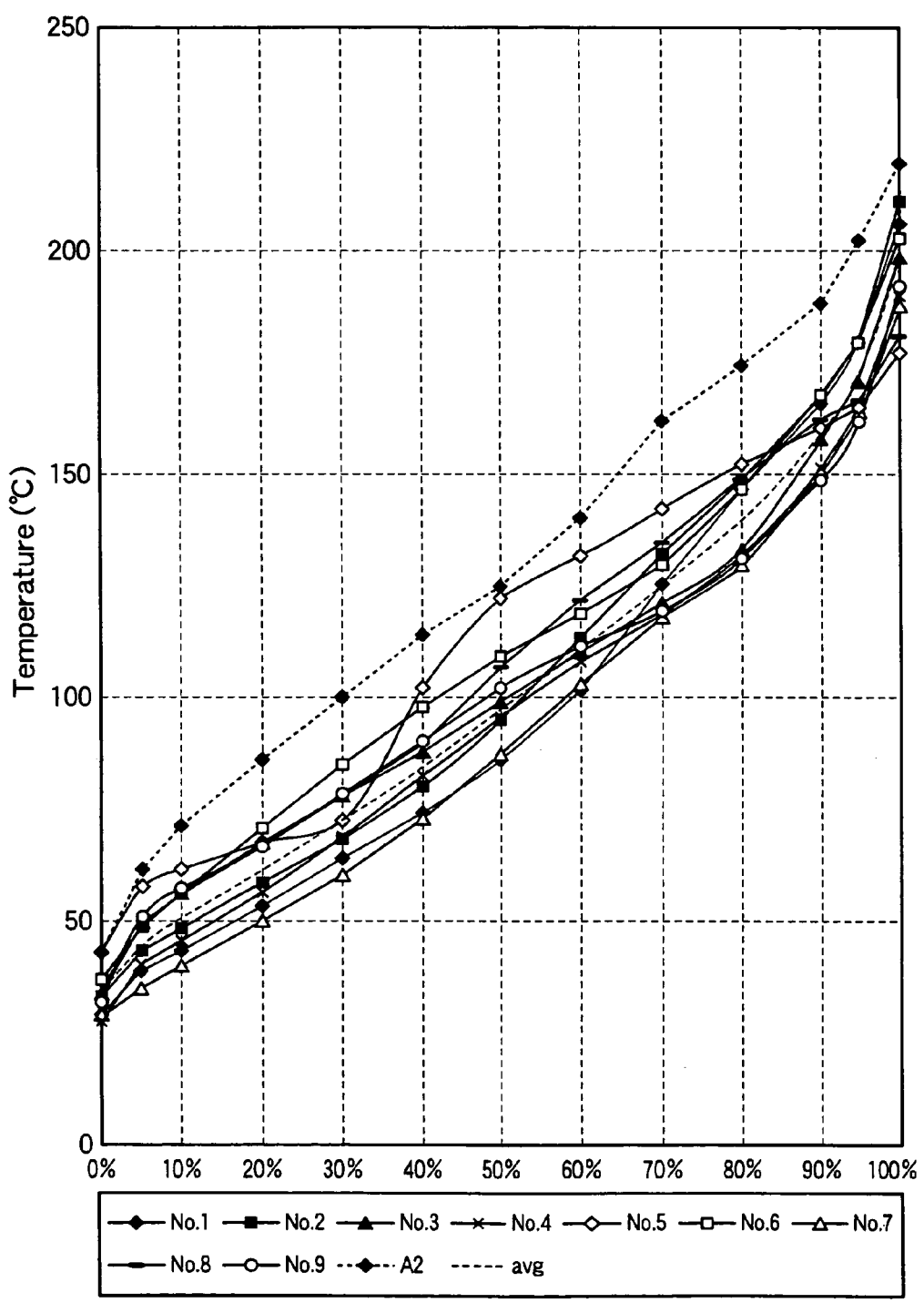
FIG. 29 is a graph showing the distillation characteristics of a gasoline.
Figure 30:
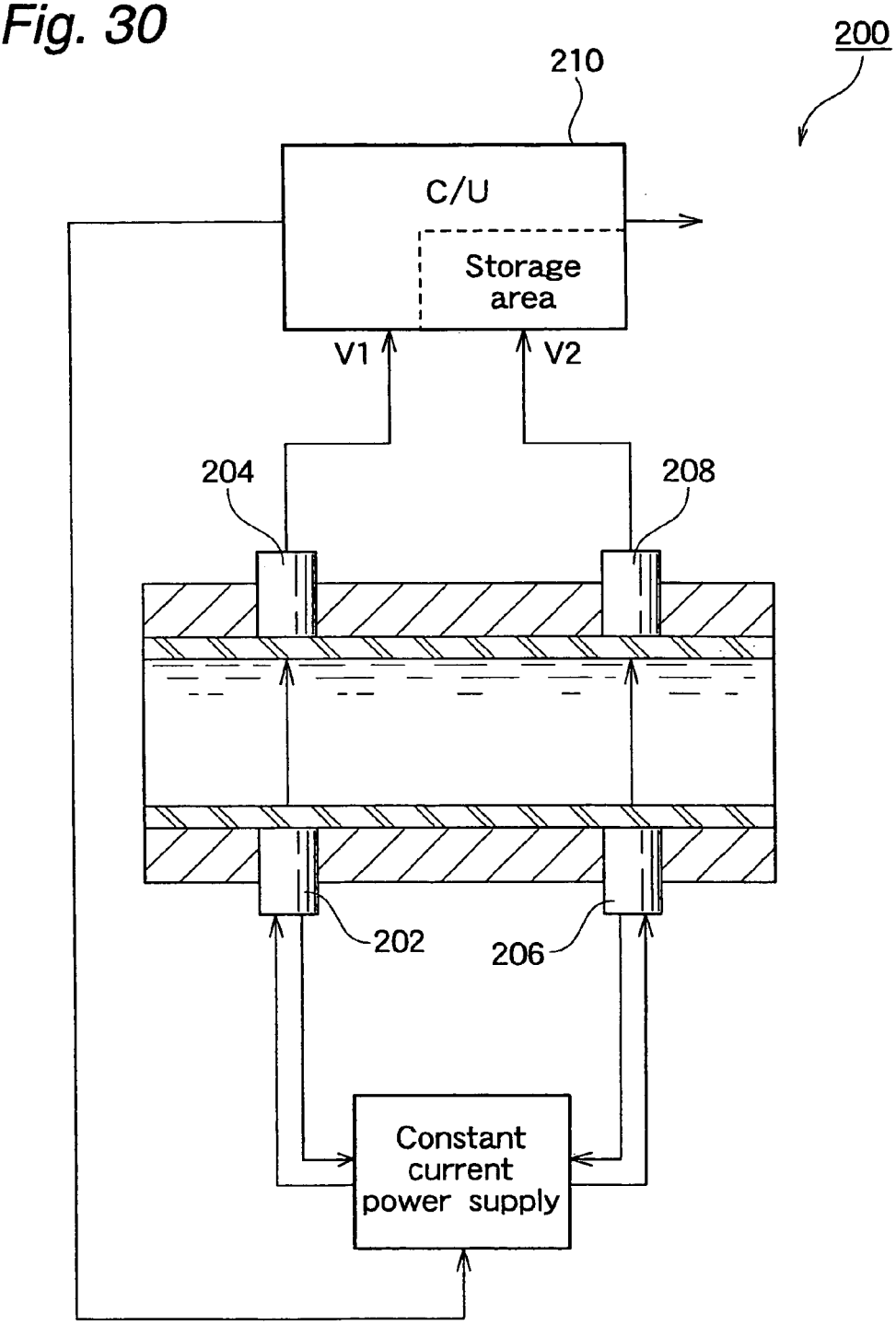
FIG. 30 is a schematic view showing a conventional optical alcohol concentration measuring apparatus.
Figure 31:
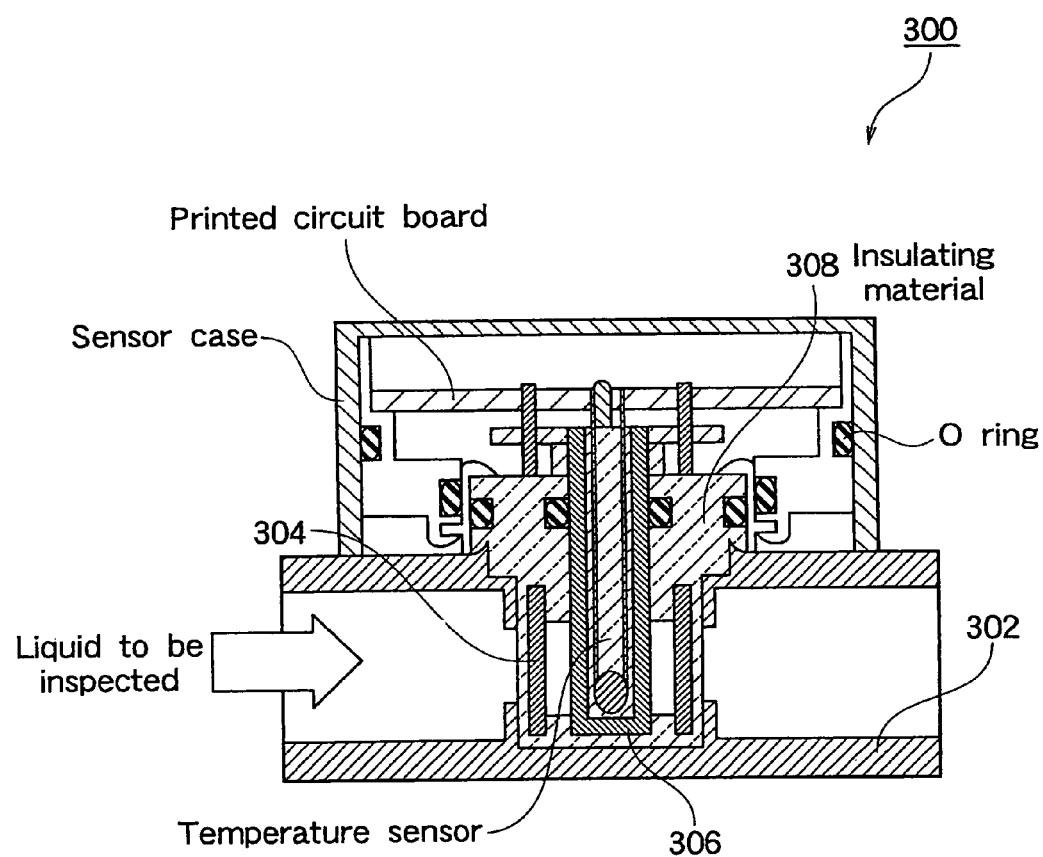
FIG. 31 is a sectional view showing a conventional electrostatic capacitance type alcohol concentration sensor.

FIG. 26 is the same schematic diagram as FIG. 28, illustrating an example in which the apparatus 10 for identifying the liquid type of a gasoline having such a structure is applied to a car system.

The same components as those in FIG. 28 have the same reference numerals and detailed description thereof will be omitted.

In a car system 100, the apparatus 10 for identifying the liquid type of a gasoline is provided in a gasoline tank 108 or on the upstream side of a gasoline pump 110.

The apparatus 10 for identifying the liquid type of a gasoline identifies the liquid type of a gasoline in the gasoline tank 108 or on the upstream or downstream side of the gasoline pump 110 (the case of the upstream side will be described in the present example for convenience of explanation) and regulates an ignition timing by an ignition timing control device 122 under the control of a control device 120 depending on the type of the gasoline.

More specifically, in the case in which the light gasoline No. 7 (which easily evaporates) is identified, for example, the ignition timing is controlled to be quickened. To the contrary, in the case in which the heavy gasoline A2 (which rarely evaporates) is identified, the ignition timing is controlled to be delayed.

Consequently, it is also possible to reduce the amount of HC in an exhaust gas and to enhance a mileage without decreasing a torque, particularly, at time of engine starting in which an engine and a catalytic device do not warm up.

Figure 27:
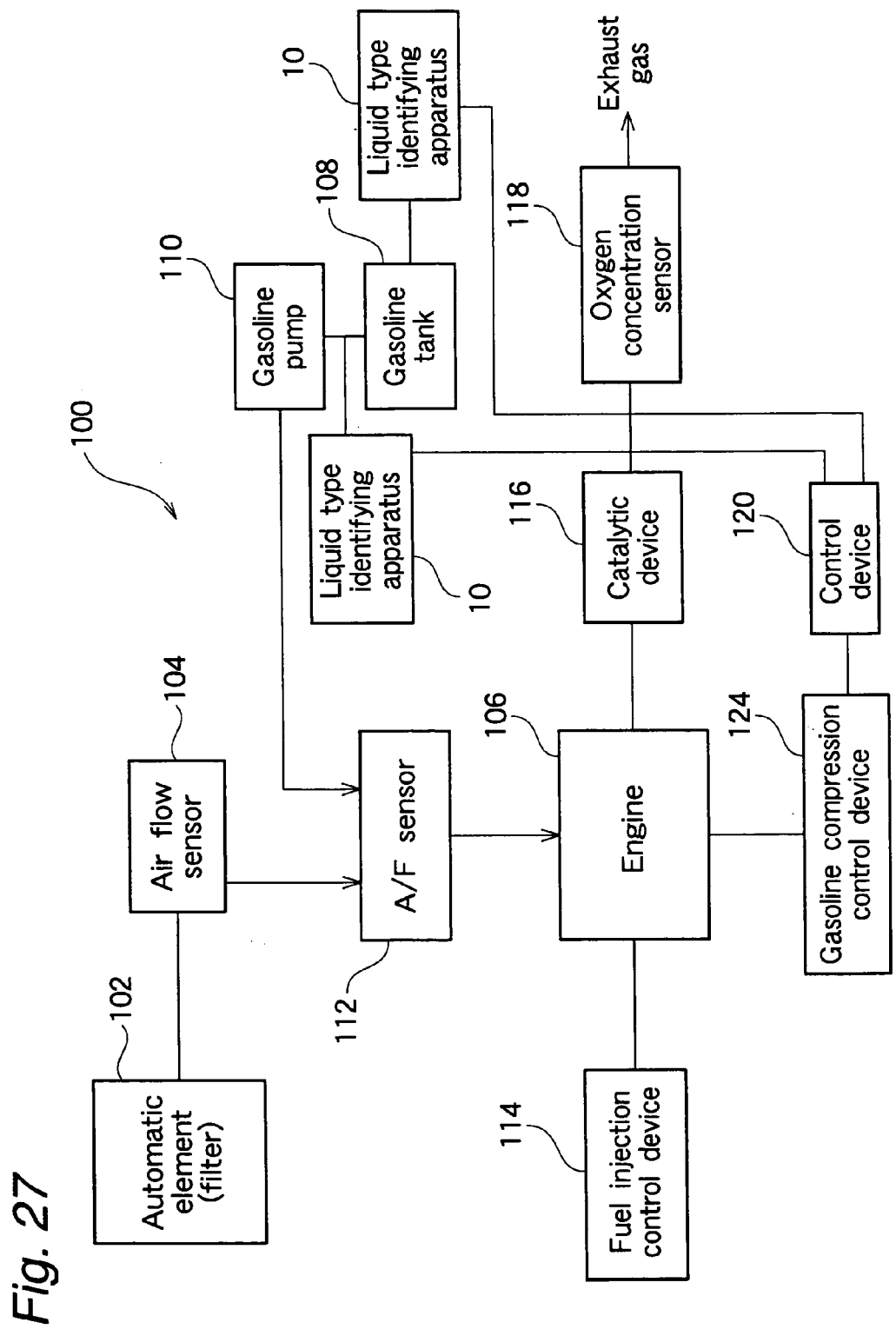
FIG. 27 is the same schematic diagram as FIG. 28, illustrating an example in which the apparatus 10 for identifying the liquid type of a gasoline according to the present invention is applied to the car system.

FIG. 27 is the same schematic diagram as FIG. 28, illustrating an example in which the apparatus 10 for identifying the liquid type of a gasoline having such a structure is applied to a car system.

The same components as those in FIG. 28 have the same reference numerals and detailed description thereof will be omitted.

In a car system 100, the apparatus 10 for identifying the liquid type of a gasoline is provided in a gasoline tank 108 or on the upstream side of a gasoline pump 110.

The apparatus 10 for identifying the liquid type of a gasoline identifies the liquid type of a gasoline in the gasoline tank 108 or on the upstream or downstream side of the gasoline pump 110 (the case of the upstream side will be described in the present example for convenience of explanation) and regulates the compressibility of the gasoline by a gasoline compression control device 124 under the control of a control device 120 depending on the type of the gasoline.

More specifically, in the case in which the light gasoline No. 7 (which easily evaporates) is identified, for example, the compressibility is controlled to be reduced. To the contrary, in the case in which the heavy gasoline A2 (which rarely evaporates) is identified, the compressibility is controlled to be increased.

Consequently, it is also possible to reduce the amount of HC in an exhaust gas and to enhance a mileage without decreasing a torque, particularly, at time of engine starting in which an engine and a catalytic device do not warm up.

While the preferred examples of the present invention have been described above, the present invention is not restricted thereto but various changes can be made without departing from the objects of the present invention, for example, a pulse voltage P, the number of sampling operations and the like can be changed properly.

According to the present invention, it is sufficient that a pulse voltage is simply applied for a predetermined time. Consequently, it is possible to identify the type of a gasoline accurately and rapidly through heating for a short time without carrying out the heating to such a temperature as to ignite the gasoline.

More specifically, there are utilized the correlation of the kinetic viscosity of the gasoline with a sensor output, a natural convection, and furthermore, an applied voltage having one pulse. Therefore, it is possible to identify the type of the gasoline accurately and rapidly.

According to the present invention, moreover, it is possible to accurately obtain a voltage output difference V0 based on the average value of sampling at a predetermined number of times for the applied voltage having one pulse. Consequently, it is possible to identify the type of the gasoline accurately and rapidly.

According to the present invention, furthermore, the type of the gasoline is identified with the voltage output difference V0 obtained for the identified gasoline based on calibration curve data to be the correlation of a voltage output difference with a temperature for a predetermined reference gasoline which is prestored. Therefore, it is possible to identify the type of the gasoline more accurately and rapidly.

According to the present invention, moreover, a liquid type voltage output Vout for the voltage output difference V0 at the measuring temperature of the identified gasoline is correlated with the output voltage for the voltage output difference at the measuring temperature for a predetermined threshold reference gasoline and is thus corrected. Consequently, it is possible to eliminate the influence of the temperature on the voltage output difference V0, thereby giving the correlation of the liquid type voltage output Vout with the characteristics of the gasoline more accurately. Thus, it is possible to identify the type of the gasoline further accurately and rapidly.

According to the present invention, furthermore, a mechanism portion for carrying out a mechanical operation is not present. Therefore, a defective operation can be prevented from being caused by a deterioration with the passage of time, foreign matters in the gasoline or the like. Thus, it is possible to identify the liquid type of the gasoline accurately and rapidly.

In addition, a sensor portion can be constituted to be very small-sized. Consequently, it is possible to identify the liquid type of the gasoline accurately with a very excellent thermal responsiveness.

According to the present invention, moreover, the heater of the liquid type identifying sensor heater, the identifying liquid temperature sensor and the liquid temperature sensor do not directly come in contact with the identified gasoline. Therefore, a defective operation can be prevented from being caused by a deterioration with the passage of time, foreign matters in the gasoline or the like. Thus, it is possible to identify the liquid type of the gasoline accurately and rapidly.

In addition, according to the present invention, based on the alcohol concentration detected by the alcohol concentration detecting device, the liquid type identification data in the identification control portion are corrected on the basis of alcohol concentration data which are prestored in the identification control portion so that the liquid type is identified. Therefore, it is possible to identify the type of the gasoline more accurately and rapidly.

According to the present invention, moreover, it is possible to reduce a distance between the electrodes by using an electrode wiring pattern formed on a base material resin film. As is apparent from the Equation 2, therefore, an electrostatic capacitance $C_s$ can be increased so that the excellent result of the measurement can be obtained.

In addition, the alcohol concentration detecting sensor is constituted by the base material resin film, the electrode wiring pattern formed on the base material resin film, and the insulating resin covering the surface of the electrode wiring pattern. Therefore, a sensor itself is flexible, thin, very small and compact, and can be installed everywhere so that the degree of freedom of a design can be increased.

Furthermore, the surface of the electrode wiring pattern is covered with the insulating resin. Therefore, an insulation between the electrodes is excellent and is not influenced by a moisture, and shielding can be carried out in order to prevent the influence of an electromagnetic wave generated from the body of a car or the like, and furthermore, an accurate measurement for the alcohol concentration can be executed.

According to the present invention, moreover, it is possible to obtain an electrode wiring pattern having a very small distance between the electrodes, for example, within a range of approximately 5 μm to 50 μm by etching. Therefore, the electrostatic capacitance $C_s$ can be increased so that the excellent result of the measurement can be obtained.

According to the present invention, furthermore, it is possible to reduce a distance between the electrodes by using the electrode wiring pattern formed on the substrate. As is apparent from the Equation 2 described above, therefore, the electrostatic capacitance $C_s$ can be increased so that the excellent result of the measurement can be obtained.

In addition, the alcohol concentration detecting sensor is constituted by the substrate, the electrode wiring pattern formed on the substrate, and the insulating coat covering the surface of the electrode wiring pattern. Therefore, the sensor itself is thin, very small and compact, and can be installed everywhere so that the degree of freedom of a design can be increased.

Moreover, the surface of the electrode wiring pattern is covered with the insulating coat. Therefore, an insulation between the electrodes is excellent and is not influenced by a moisture, and shielding can be carried out in order to prevent the influence of an electromagnetic wave generated from the body of a car or the like, and furthermore, an accurate measurement for the alcohol concentration can be executed.

According to the present invention, furthermore, it is possible to obtain an electrode wiring pattern having a thickness of 0.1 to 5 μm by sputtering at a very small distance between the electrodes, for example, within a range of approximately 5 μm to 50 μm by the sputtering. Therefore, the electrostatic capacitance $C_s$ can be increased so that the excellent result of the measurement can be obtained.

According to the present invention, moreover, it is possible to obtain, by chemical vapor deposition (CVD), a very minute and thin insulating coat which is not influenced by a gasoline such as a gasoline or alcohol, for example, $SiO_2$, $Al_2O_3$ or the like. Thus, the sensor itself can be thin, very small and compact.

Furthermore, the electrode does not directly come in contact with the gasoline. Therefore, a defective operation can be prevented from being caused by a deterioration with the passage of time, foreign matters in the gasoline or the like. Thus, it is possible to detect the alcohol concentration accurately and rapidly.

In addition, the substrate is provided. Therefore, it is easy to assemble and attach the alcohol concentration detecting sensor into the apparatus.

According to the present invention, moreover, the positive and negative electrodes which are comb-toothed are formed to be alternately intricate. Therefore, the electrodes having a very small distance therebetween can be provided to be compact as a whole.

Accordingly, it is possible to obtain an electrode wiring pattern having a very small distance between the electrodes, for example, within a range of approximately 5 μm to 50 μm by etching and sputtering, respectively. Therefore, the electrostatic capacitance Cs can be increased so that the excellent result of the measurement can be obtained.

According to the present invention, furthermore, the alcohol concentration in the gasoline can be detected accurately and rapidly, and it is possible to control a torque to be constant by excessively adding a gasoline corresponding to the amount of addition of alcohol, for example, ethanol as an antiknocking agent.

According to the present invention, furthermore, it is possible to identify the type of the gasoline in a car accurately and rapidly and to regulate an ignition timing based on the result of the identification of the type of the gasoline. Consequently, it is possible to obtain a proper ignition timing depending on the type of the gasoline.

According to the present invention, furthermore, it is possible to identify the type of the gasoline in a car accurately and rapidly and to regulate the compressibility of the gasoline based on the result of the identification of the type of the gasoline. Consequently, it is possible to obtain a proper compressibility of the gasoline depending on the type of the gasoline.

Therefore, it is also possible to reduce the amount of HC in an exhaust gas and to enhance a mileage without decreasing a torque, particularly, at time of engine starting in which an engine and a catalytic device do not warm up. Thus, the present invention can produce various remarkable and peculiar functions and effects, which is very excellent.

The invention claimed is:

1. An apparatus for identifying a liquid type of a gasoline, comprising:

a gasoline liquid type identifying chamber for causing an identified gasoline introduced into a liquid type identifying apparatus body to stay temporarily;

a liquid type identifying sensor heater provided in the gasoline liquid type identifying chamber; and a liquid temperature sensor provided in the gasoline liquid type identifying chamber apart from the liquid type identifying sensor heater at a constant interval;

the liquid type identifying sensor heater including a heater and an identifying liquid temperature sensor provided in the vicinity of the heater, the apparatus further comprising an identification control portion for applying a pulse voltage to the liquid type identifying sensor heater for a predetermined time, heating the identified gasoline staying temporarily in the gasoline liquid type identifying chamber by the heater and identifying the liquid type with a voltage output difference V0 corresponding to a temperature difference between an initial temperature and a peak temperature in the identifying liquid temperature sensor, and an alcohol content detecting chamber, the alcohol content detecting chamber being provided with an alcohol concentration detecting device in which an alcohol concentration in the gasoline is detected by introducing a gasoline between electrodes of an alcohol concentration detecting sensor, and by measuring a change in a specific inductive capacity of the gasoline between the electrodes with an oscillation frequency, and based on the alcohol concentration detected by the alcohol concentration detecting device, liquid type identification data in the identification control portion being corrected on the basis of alcohol concentration data which are prestored in the identification control portion, thereby identifying a liquid type.

2. The apparatus for identifying a liquid type of a gasoline according to claim 1, wherein the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $$V0=V2-V1.$$

3. The apparatus for identifying a liquid type of a gasoline according to claim 1, wherein in accordance with calibration curve data to be a correlation of a voltage output difference with a temperature for a predetermined reference gasoline prestored in the identification control portion, the identification control portion is constituted to identify a type of a gasoline with the voltage output difference V0 obtained for the identified gasoline.

4. The apparatus for identifying a liquid type of a gasoline according to claim 1, wherein the identification control portion is constituted to correlate a liquid type voltage output Vout for the voltage output difference V0 at a measuring temperature of the identified gasoline with an output voltage for a voltage output difference at a measuring temperature for a predetermined threshold reference gasoline and to thus carry out a correction.

5. The apparatus for identifying a liquid type of a gasoline according to claim 1, wherein the liquid type identifying sensor heater is a laminated liquid type identifying sensor heater in which a heater and an identifying liquid temperature sensor are laminated through an insulating layer.

6. The apparatus for identifying a liquid type of a gasoline according to claim 1, wherein the heater and the identifying liquid temperature sensor in the liquid type identifying sensor heater are constituted to come in contact with the identified gasoline through a metallic fin, respectively.

7. The apparatus for identifying a liquid type of a gasoline according to claim 1, wherein the liquid temperature sensor is constituted to come in contact with the identified gasoline through the metallic fin.

8. The apparatus for identifying a liquid type of a gasoline according to claim 1, wherein the alcohol concentration detecting sensor comprises an alcohol concentration detecting sensor body including a base material resin film, an electrode wiring pattern formed on the base material resin film, and an insulating resin covering a surface of the electrode wiring pattern.

9. The apparatus for identifying a liquid type of a gasoline according to claim 8, wherein the alcohol concentration detecting sensor body is stuck onto a substrate.

10. The apparatus for identifying a liquid type of a gasoline according to claim 8, wherein the electrode wiring pattern is obtained by selectively etching a conductive metallic foil laminated on one of surfaces of the base material resin film, thereby forming a wiring pattern taking a predetermined shape.

11. The apparatus for identifying a liquid type of a gasoline according to claim 1, wherein the alcohol concentration detecting sensor comprises a substrate, an electrode wiring pattern formed on the substrate, and an insulating coat covering a surface of the electrode wiring pattern.

12. The apparatus for identifying a liquid type of a gasoline according to claim 11, wherein the electrode wiring pattern is obtained by selectively etching a conductive metallic thin film formed on one of surfaces of the substrate by sputtering, thereby forming a wiring pattern taking a predetermined shape.

13. The apparatus for identifying a liquid type of a gasoline according to claim 11, wherein the insulating coat is formed by chemical vapor deposition (CVD).

14. The apparatus for identifying a liquid type of a gasoline according to claim 8, wherein the electrode wiring pattern has such a shape that positive and negative electrodes which are comb-toothed are alternately intricate.

15. An apparatus for identifying a liquid type of a gasoline of a car,
wherein the apparatus for identifying a liquid type of a gasoline according to claim 1 is provided in a gasoline tank or on an upstream side or a downstream side of a gasoline pump.

16. An apparatus for reducing an exhaust gas of a car, comprising:
the apparatus for identifying a liquid type of a gasoline according to claim 1 which is provided in a gasoline tank or on an upstream side or a downstream side of a gasoline pump; and
an ignition timing control device for regulating an ignition timing based on the type of the gasoline which is identified by the apparatus for identifying a liquid type of a gasoline.

17. An apparatus for reducing an exhaust gas of a car, comprising:
the apparatus for identifying a liquid type of a gasoline according to claim 1 which is provided in a gasoline tank or on an upstream side or a downstream side of a gasoline pump; and
a gasoline compression control device for regulating a compressibility of the gasoline based on the type of the gasoline which is identified by the apparatus for identifying a liquid type of a gasoline.

18. A method for identifying a liquid type of a gasoline, comprising the steps of:
applying a pulse voltage for a predetermined time to a liquid type identifying sensor heater including a heater and an identifying liquid temperature sensor provided in the vicinity of the heater; heating an identified gasoline by the heater; and identifying the liquid type with a voltage output difference V0 corresponding to a temperature difference between an initial temperature and a peak temperature in the identifying liquid temperature sensor;
introducing a gasoline between electrodes of an alcohol concentration detecting sensor, and measuring a change in a specific inductive capacity of the gasoline between the electrodes with an oscillation frequency thereby detecting an alcohol concentration in the gasoline; and
wherein based on the alcohol concentration detected by the alcohol concentration detecting device, correcting liquid type identification data in the identification control portion on the basis of alcohol concentration data which are prestored in the identification control portion, thereby identifying a liquid type.

19. The method for identifying a liquid type of a gasoline according to claim 18, wherein the voltage output difference V0 is equal to a voltage difference between an average initial voltage V1 obtained by sampling an initial voltage before application of the pulse voltage at a predetermined number of times and an average peak voltage V2 obtained by sampling a peak voltage after the application of the pulse voltage at a predetermined number of times, that is, $$V0=V2-V1.$$

20. The method for identifying a liquid type of a gasoline according to claim 18, wherein in accordance with calibration curve data to be a correlation of a voltage output difference with a temperature for a predetermined reference gasoline which is prestored, a type of a gasoline is identified with the voltage output difference V0 obtained for the identified gasoline.

21. The method for identifying a liquid type of a gasoline according to claim 18, wherein a liquid type voltage output Vout for the voltage output difference V0 at a measuring temperature of the identified gasoline is correlated with an output voltage for a voltage output difference at a measuring temperature for a predetermined threshold reference gasoline and is thus corrected.

22. The method for identifying a liquid type of a gasoline according to claim 18, wherein the liquid type identifying sensor heater is a laminated liquid type identifying sensor heater in which a heater and an identifying liquid temperature sensor are laminated through an insulating layer.

23. The method for identifying a liquid type of a gasoline according to claim 18, wherein the heater and the identifying liquid temperature sensor in the liquid type identifying sensor heater are constituted to come in contact with the identified gasoline through a metallic fin, respectively.

24. The method for identifying a liquid type of a gasoline according to claim 18, wherein the liquid temperature sensor is constituted to come in contact with the identified gasoline through the metallic fin.

25. The method for identifying a liquid type of a gasoline according to claim 18, wherein the alcohol concentration detecting sensor comprises an alcohol concentration detecting sensor body including a base material resin film, an electrode wiring pattern formed on the base material resin film, and an insulating resin covering a surface of the electrode wiring pattern.

26. The method for identifying a liquid type of a gasoline according to claim 25, wherein the alcohol concentration detecting sensor body is stuck onto a substrate.

27. The method for identifying a liquid type of a gasoline according to claim 25, wherein the electrode wiring pattern is obtained by selectively etching a conductive metallic foil laminated on one of surfaces of the base material resin film, thereby forming a wiring pattern taking a predetermined shape.

28. The method for identifying a liquid type of a gasoline according to claim 18, wherein the alcohol concentration detecting sensor comprises a substrate, an electrode wiring pattern formed on the substrate, and an insulating coat covering a surface of the electrode wiring pattern.

29. The method for identifying a liquid type of a gasoline according to claim 28, wherein the electrode wiring pattern is obtained by selectively etching a conductive metallic thin film formed on one of surfaces of the substrate by sputtering, thereby forming a wiring pattern taking a predetermined shape.

30. The method for identifying a liquid type of a gasoline according to claim 28, wherein the insulating coat is formed by chemical vapor deposition (CVD).

31. The method for identifying a liquid type of a gasoline according to claim 25, wherein the electrode wiring pattern has such a shape that positive and negative electrodes which are comb-toothed are alternately intricate.

32. A method for identifying a liquid type of a gasoline of a car, comprising the step of:
identifying a type of a gasoline in a gasoline tank or on an upstream side or a downstream side of a gasoline pump by using the method for identifying a liquid type of a gasoline according to claim 15.

33. A method for reducing an exhaust gas of a car, comprising the steps of:
identifying a type of a gasoline in a gasoline tank or on an upstream side or a downstream side of a gasoline pump by using the method for identifying a liquid type of a gasoline according to claim 18; and
regulating an ignition timing based on the type of the gasoline which is identified by the apparatus for identifying a liquid type of a gasoline.

34. A method for reducing an exhaust gas of a car, comprising the steps of:
identifying a type of a gasoline in a gasoline tank or on an upstream side or a downstream side of a gasoline pump by using the method for identifying a liquid type of a gasoline according to claim 18; and
regulating a compressibility of the gasoline based on the type of the gasoline which is identified by the apparatus for identifying a liquid type of a gasoline.

* * * * *

UNITED STATES PATENT AND TRADEMARK OFFICE
CERTIFICATE OF CORRECTION

PATENT NO. : 7,168,300 B2  
APPLICATION NO. : 10/529796  
DATED : January 30, 2007  
INVENTOR(S) : Kawanishi et al.

Page 1 of 1

It is certified that error appears in the above-identified patent and that said Letters Patent is hereby corrected as shown below:

<u>Column 7</u>, Line 63, "of surfaces" should read -- of the surfaces --

<u>Column 11</u>, Lines 40-41
"BEST MODE FOR CARRYING OUT DETAILED DESCRIPTION OF THE INVENTION"
should read
-- DETAILED DESCRIPTION OF THE INVENTION --

<u>Column 12</u>, Line 36, "into direct in contact" should read -- into direct contact --

<u>Column 28</u>, Line 23, Claim 32, "according to claim 15" should read -- according to claim 18 --

Signed and Sealed this

Twenty-sixth Day of June, 2007

JON W. DUDAS  
*Director of the United States Patent and Trademark Office*